(12) United States Patent
Levengood et al.

(10) Patent No.: US 6,347,238 B1
(45) Date of Patent: Feb. 12, 2002

(54) METHOD AND APPARATUS FOR DETECTING, RECORDING AND ANALYZING SPONTANEOUSLY GENERATED TRANSIENT ELECTRIC CHARGE PULSES IN LIVING ORGANISMS

(76) Inventors: William C. Levengood, 4853 Wolf Lake Rd., Grass Lake, MI (US) 49240; John L. Gedye, 2140 W. Maple Rd., Bloomfield Hills, MI (US) 48301

( * ) Notice: Subject to any disclaimer, the term of this patent is extended or adjusted under 35 U.S.C. 154(b) by 0 days.

(21) Appl. No.: 09/453,705

(22) Filed: Dec. 3, 1999

Related U.S. Application Data
(60) Provisional application No. 60/110,706, filed on Dec. 3, 1998.

(51) Int. Cl.[7] ............................................. A61B 5/04
(52) U.S. Cl. ...................... 600/372; 600/547; 600/548; 600/554
(58) Field of Search ................................ 600/372, 389, 600/544, 546, 547, 548, 551, 554, 557; 128/878

(56) References Cited

U.S. PATENT DOCUMENTS 4,697,599 A * 10/1987 Woodley et al. ............ 600/547
6,088,615 A * 7/2000 Masuo ........................ 600/547
6,167,299 A * 12/2000 Galchenkov et al. ....... 600/547

FOREIGN PATENT DOCUMENTS

RU    WO 97/45162    * 12/1997 ................. 600/547

* cited by examiner

Primary Examiner—Linda C. M. Dvorak
Assistant Examiner—David M. Ruddy
(74) Attorney, Agent, or Firm—Alfred M. Walker

(57) ABSTRACT

A method and apparatus is provided for detecting and recording a specific type of electric pulse induced in metal electrodes by the living tissue of humans, other animals or plants, and by certain organic and inorganic models of such living tissue. The purely passive system detects the electric energy produced by the living source as it interacts with the crystalline lattice of conductive metal electrodes to produce a train of oscillating pulses, the amplitude of whose envelope decays as a linear function of log-time. Specific aspects of these pulses can be used to study the state of the living, or non-living, source and to detect changes in this state over time. The results of such studies of living sources can be interpreted, respectively, in terms of the state of health, or disease, of the source and of changes in the state of health, or disease, of the source, and can thus be used to recognize, characterize and evaluate conditions of the living organism and to quantify the effects of therapies and putative therapies.

10 Claims, 21 Drawing Sheets

Polarity effects in CDP responses from a living plant (Impatiens spp.) stem about 30 cm long and 2 cm diameter. A) basipetal (bottom) end of stem on outer surface of cathode plate, acropetal (top) on anode. B) basipetal anode, acropetal cathode.

CDP Subject - GL - before and after Chiropractic Treatments
by Dr. Tom Kopinski, Kalamazoo, MI

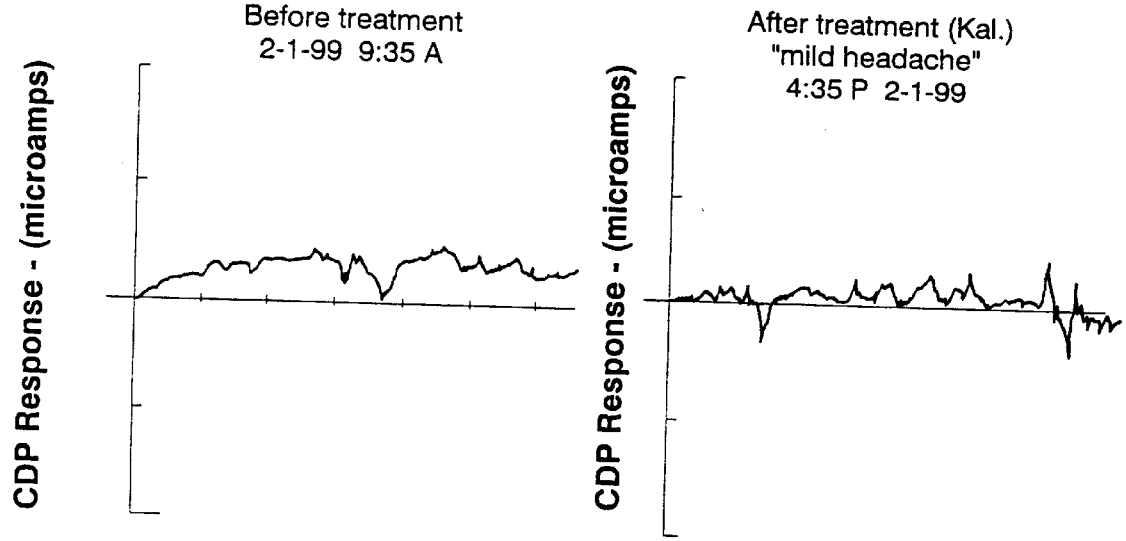
FIG. 12E
FIG. 12F
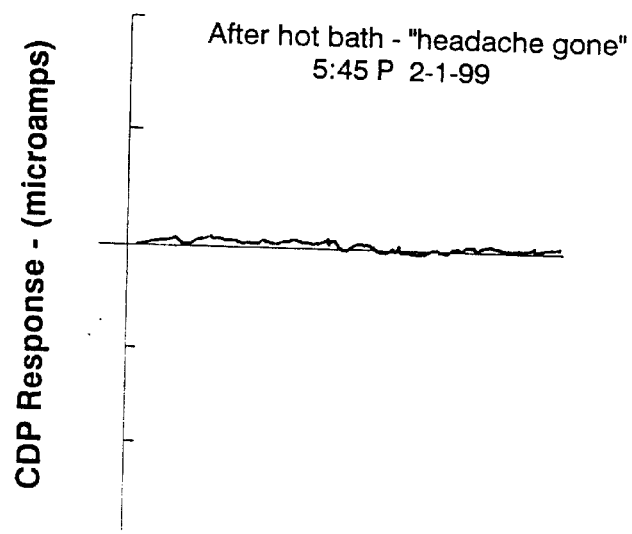
FIG. 12G

CDP subject - GL - Pain Conditions

Influence of Interactive Biofield Energy (IBE) on CDP responses
(subject GM 4-6-98)

Fibromyalgia - "Pain"
11:10 A Before IBE
(note negative pulses)

Immediately after IBE
12:00 N Felt tingling
in fingers.
(note shift toward base
line & fewer neg. pulses)

45 min. after IBE
12:45 P "feels no pain"
(note shift <u>above</u> base
line & positive pulses.)

FIG. 17A
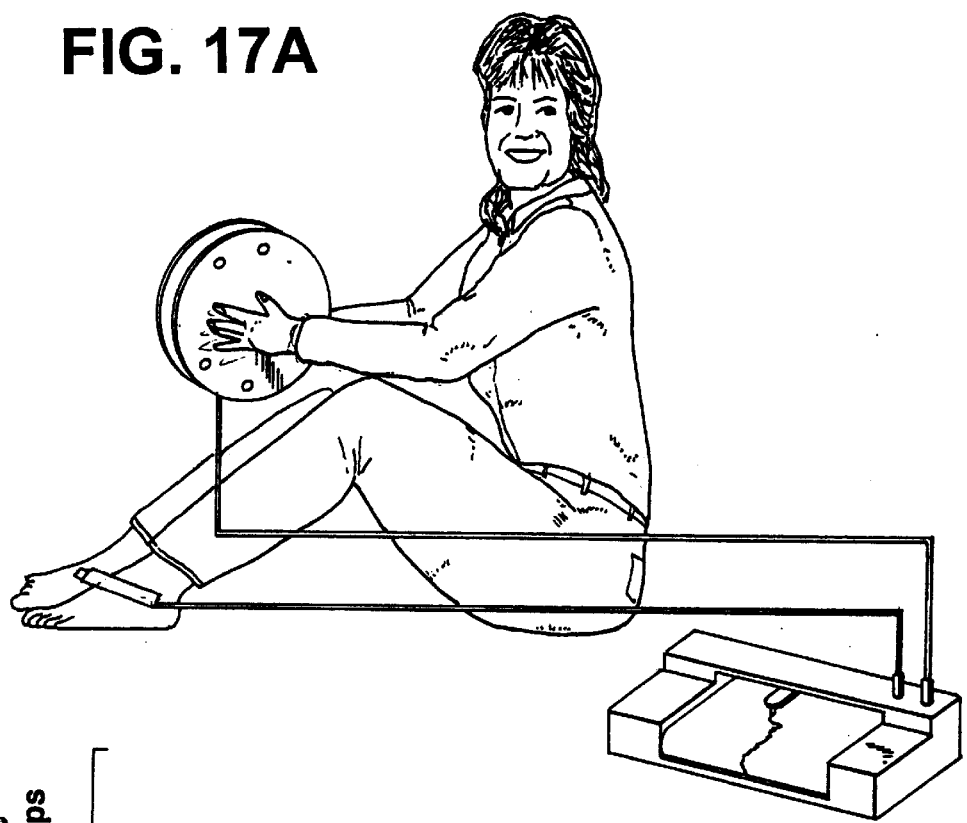
FIG. 17B
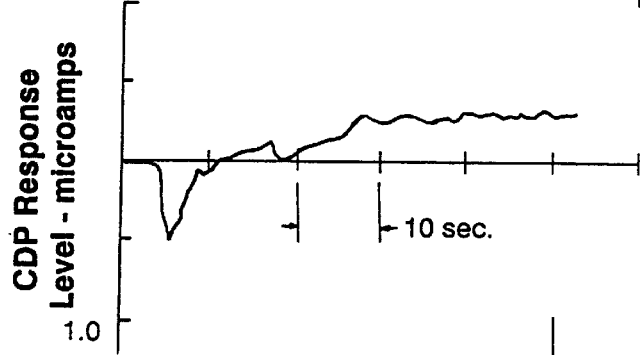
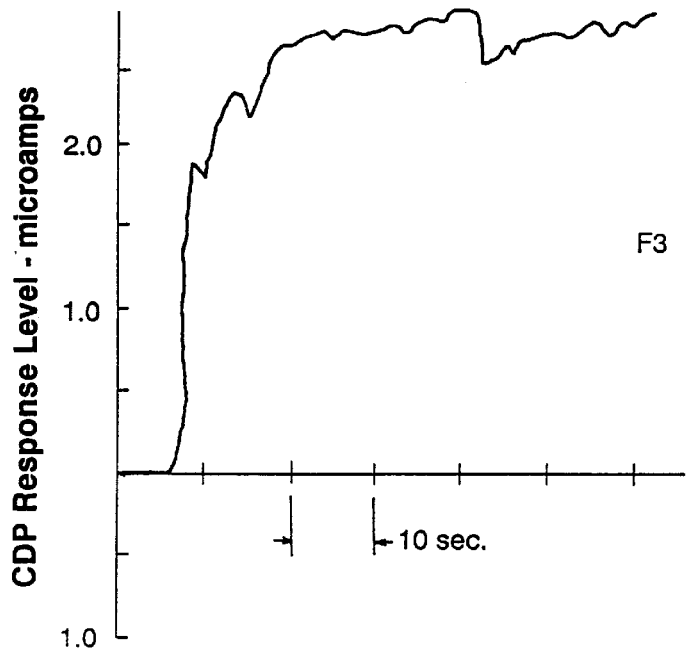
FIG. 17C

METHOD AND APPARATUS FOR DETECTING, RECORDING AND ANALYZING SPONTANEOUSLY GENERATED TRANSIENT ELECTRIC CHARGE PULSES IN LIVING ORGANISMS

RELATED APPLICATIONS

This application is based on provisional application Serial No. 60/110,706, filed Dec. 3, 1998.

FIELD OF THE INVENTION

The present invention relates to studying the state of living organisms.

BACKGROUND OF THE INVENTION

Recognizing, characterizing and evaluating pain in animals, including humans, is a largely subjective activity due to the lack of generally accepted objective criteria for recognizing, characterizing and evaluating the altered state of an animal, such as a human or other animal, in pain. Likewise, in botany, it is often difficult to measure when an edible plant is still edible with firm tissues and is not wilted. It is therefore difficult to provide a non-living model of living systems, which can be quantitatively evaluated.

There are precedents in physiology for the concept of non-living models of living systems. Many examples can be found in the work of J. C. Bose who, at the beginning this century, drew the attention of physiologists to the similarity of certain electrical responses in metals and muscle tissue. Another well-known example of a non-living model is the "iron wire" model of nerve impulse conduction.

In investigating the bioelectric attributes of living systems with pairs of electrodes connected to some kind of amplifying and recording system it has been traditional to work operationally in two stages: an initial stage in which the electrodes are appropriately positioned in relation to the tissue to be studied, followed by a recording stage after bioelectric effects arising during the positioning of the electrodes have largely dissipated.

Any residual bioelectric effects are often referred to by using such terms as "noise", "interference", or "non-linearity", the key point being that these are traditionally unwelcome barriers to the desired ideal steady state condition. (Faupel, U.S. Pat. No. 5,715,821).

The essence of the present invention, in contrast, is to focus on, and follow the time course of, the bioelectric disturbance that arises consequent to the second electrode being brought into proximity, or, more usually, contact with the relevant tissue site.

Various types of electrodes have previously been used to measure bioelectric attributes of the human organism in the form of voltage potentials or electric currents.

Some of these have employed an electric current introduced into the electrodes, such as with a galvanic skin response and others which can only measure the organism's interaction with the introduced current and not the current produced directly by the organism. Hirschowitz, (U.S. Pat. No. 4,328,809) first filters out as noise the kind of rapidly changing signals, which are at the heart of the present invention, and then uses a single value, which is arrived at by averaging the 180 readings, to represent the measurement.

Other methods have been passive but have limited themselves to measuring the strength of the external electrostatic field (Hoogendoorn, U.S. Pat. No. 4,602,639) or to producing a simple numerical value of the voltage potential (Faupel, U.S. Pat. Nos. 4,995,383 and 5,099,844; Conway, U.S. Pat. Nos. 4,557,273 and 4,321,360), differences between minimum and maximum voltages (Faupel, U.S. Pat. No. 5,715,821; Stoller, U.S. Pat. No. 4,557,271), differences between voltages at two different points or measurements of simple electric current (Alexeev, U.S. Pat. No. 5,409,011).

Many are designed to look at only specific body functions such as the brain (Zhang, U.S. Pat. No. 5,144,554; Kiyuna, U.S. Pat. No. 5,785,653), the gastrointestinal system (Zhang, U.S. Pat. No. 5,144,554) or ovulation (Stoller, U.S. Pat. No. 4,557,273; Conway, U.S. Pat. No. 4,312,360).

Still others have used extremely expensive Superconducting Quantum Interference devices or "SQUIDS" (Takeda, U.S. Pat. No. 5,646,526; Abraham-Fuchs, U.S. Pat. No. 5,417,211) which are extremely expensive and do not detect the types of pulses described in the inexpensive and easy-to-use system of the present invention.

Some have detected waves such as electrocardiograph (EKG) waves, electroencephalograph (EEG) waves or square waves, but not the unique pulses described herein.

The aforementioned methods of analyzing data from other electrode systems have largely concentrated on eliminating irregular, non-periodic fluctuations that comprise the essential data of the present system, considering irregular fluctuations as noise to be averaged out, smoothed out, or filtered out (Hirschowitz, U.S. Pat. No. 4,328,809; Faupel, U.S. Pat. No. 5,715,821).

Japanese researchers (Seto et al, "Detection of extraordinary large biomagnetic field strength from human hand during external QI emission," *International Journal of Acupuncture and Electro-Therapeutics Research*, V. 17 pp. 75–94 (1992)) used an 80,000 turn solenoid experimental probe coil sensitive to electromagnetic fluctuations to measure pulses emanating from the hands of Qi Gong masters. They calculated the amount of electrical energy needed to produce pulses of that size and showed that it exceeds the carrying capacity of the nerves of the arm, thereby excluding nerve signals as the sole source.

Numerous problems with artifacts limit the usefulness of such coils, as the Applicant's research showed in connection with the present invention. For example the palm must be held over the coil at a fixed interval. Any vertical fluctuation of the hand produces extraneous signals, which confuse the readings. Furthermore, many people have trouble holding their hands perfectly still for 30 seconds or more. In addition, the device is far less sensitive than the electrode system of the present invention. While Qi Gong masters produce strong, regular pulses, normal people produce only occasional tiny pulses, making the disturbing effects of movement-generated extraneous signals all the more serious. In addition, the relative lack of sensitivity means that there is far less information, which can be extracted from the signals.

In contrast, as more fully explained later herein, the physical contact with the palms and other areas of the body being measured by the system of the present invention gives much more reliable and informative readings to detect and record changes in bioelectric pulses indicative of the state of health of a human, other animal or plant.

OBJECTS OF THE INVENTION

It is therefore an object of the present invention to provide a device and method for detecting and recording specific types of bioelectric pulses, these being an aspect of the biofield of both human, other animal and plant subjects. The term "biofield" is defined in "Sections on Biofield Diagnostics and Therapeutics", *Alternative Medicine: Expanding Medical Systems and Practices in the United States*, prepared under the auspices of the Workshop on Alternative Medicine, Chantilly, Virginia, Sep. 14–16, 1992, Part I: *Field of Practice, Manual Healing Methods*, pages 134–146.

It is a further object of the present invention to provide a device for detecting changes in biofield energy levels in both animal and plant subjects. This latter has important applications in assessing the nutritional value of plant foodstuffs, both in general and in particular. This is illustrated by studies of the energy differences between fresh and wilted carrots, and the energy changes accompanying a banana ripening.

It is further an object of the present invention to enable investigators to collaboratively create libraries of CDP trace recordings, analogous to the fingerprint libraries in current use. This allows the creation of specific databases for various living tissue conditions.

For example, in a study of human subject persons with traumatic spinal injuries, in connection with the present invention, Applicants-noticed that in certain subjects the dissipative transient bioelectric disturbance recordings contained pulses occurring at a regular rate of from 1.4 to 1.7 Hz, such as, for example, 1.6 Hz. Applicant's studies revealed that all twelve (12) of the subjects who have been shown to exhibit this 1.4–1.7 Hz pulse rate had suffered some form of traumatic spinal injury at some time in the past, sometimes decades before the recording and beyond the memory of the subject. This regular pattern was not been seen in any of the fifty (50), or so, other human subjects investigated. The present invention thus provides a noninvasive, low-cost, investigatory tool for routine use in the management of trauma in general and traumatic spinal injury in particular.

It is further an object of the present invention to offer practitioners of certain therapies a means of monitoring progress in their patients and hence of assessing their own effectiveness. For example, "hands on" manipulative therapies aimed at improving the energy level of the patient are obvious candidates. Applicant's found that in a subject treated with a form of hands on healing, numerous Charge Density Pulse trace recordings taken before and after therapeutic sessions showed a general increase in energy level (as quantified by the (Pa) measured peak amplitude pulse level) following such treatment. In a subject who had been diagnosed as suffering from fibromyalgia, CDP trace recordings taken during and after episodes of severe pain and discomfort showed marked differences of waveform morphology. In a subject with a history of severe spinal trauma, CDP trace recordings taken before and after a series of chiropractic therapy sessions showed consistent increases in energy level following treatment.

Applicants found that CDP trace recordings taken before and after the ingestion of Gingko Biloba and Ginseng have, in both cases, demonstrated raised energy levels about 30 minutes after ingestion (approximately the time it takes the body to absorb the active ingredients after swallowing a capsule). These raised levels persisted for several hours. In this case, energy level was calculated by multiplying the number of individual pulses by the amplitude of the maximum pulse level following the Pa.

Applicants further found CDP trace recordings taken before and after Zazen meditation have demonstrated raised energy levels persisting for several hours.

These results demonstrate the possibility of using CDP trace recordings to provide objective documentation of the effectiveness of a variety of therapeutic approaches for which, currently, little or no readily obtainable objective evidence of effectiveness exists. This should be attractive to both insurer and insured alike.

It is clear from the Applicant's studies noted above that the Charge Density Pulse (CDP) technique allows a dissipative transient bioelectric disturbance to be recorded between any two points on the surface of the human body. Moreover, a special subset of such pairs of points, which may be expected to be of considerable importance in future studies, is when either, or both, points of the pair are recognized acupuncture points.

SUMMARY OF THE INVENTION

In keeping with these objects and others which may become apparent, the Charge Density Pulse (CDP) method discussed here provides a simple means for monitoring changes in the bioelectric field associated with living organisms, including humans and plants as discussed by the Applicants herein in Levengood, W. C. and Gedye, J. L. "Evidence for Charge Density Pulses Associated with Bioelectric Fields in Living organisms", *Subtle Energies and Energy Medicine*, V.8, No.1, pp. 33–54 (1999). The monitoring means of the present invention can be used to measure either the field of the individual organism as a whole or specific sites on the organism. For example, utilizing an electrical capacitance type monitoring system in which the bioelectric field interacts with metal collector plates, it is possible to examine details of what one defines as Charge Density Pulse (CDP) pulses generated between the electrodes and the palms of the hands or, for that matter, plants.

The polarized nature of the bioelectric fields, their specific influence on the metal electrodes interposed in the system indicate CDP interactions between metals and living tissue.

This purely passive system of the present invention uses no active input current. The biofield measured by the present invention is a continuous biofield common to the organism as a whole. Its polarity (as shown in left-right differences described herein) also distinguishes it from signals from other electrode systems.

For these reasons, the physical contact with the palms and other areas of the body provided for in the present system gives much more reliable and informative readings. As is described more fully later, there is a limit to the rate at which successive Charge Density Pulse (CDP) responses can be elicited at one site without affecting the characteristics of the response. In the case of human inter-palmar recording the refractory period is over 5 minutes duration.

There is a significant distinction between contact and non-contact electrodes. Whenever a conductive metal (or one of several other types of crystalline material) electrode is brought near to, or actually touches, the living tissue being studied, there is a contact potential-surface interaction between the electric field of the electrode and the bioelectric field of the tissue. When two such electrodes are brought near to, or actually touch, different parts of one piece of living tissue, and these electrodes are connected through a 1.0 K ohm resistor, as described in the present invention herein, the dissipative transient bioelectric disturbance described above results and can be recorded.

This is the essence of the Charge Density Pulse (CDP) device of the present invention. It does not require actual contact between the electrodes and the tissue being studied, only proximity of the electrode to the tissue; although in most currently foreseeable practical applications actual electrode-tissue contact is desirable, as it leads to more consistent results by allowing better control of the essential parameters of the electrode-tissue interfacial reaction.

With respect to one embodiment of the present invention, wherein CDP response traces are generated from a human subject by placing the palms of the hands on conductive plates having leads to a data recorder, when modified by the inclusion of a microswitch, M1, in one of the leads connecting the aluminum plates to the 1.0 K ohm resistor, and a microswitch, M2, in one of the leads connecting the 1.0 K ohm resistor to the recording device, there are four possible configurations of microswitch states, as noted in Table 1.

TABLE 1

| Configuration | Microswitch M1 | Microswitch M2 | Result |
| --- | --- | --- | --- |
| 1 | Closed | Closed | Dissipative curve - record |
| 2 | Closed | Open | Dissipative curve - no record |
| 3 | Open | Closed | No dissipative curve - record |
| 4 | Open | Open | No dissipative curve - no record |

Table 1 shows that configuration 1 is the standard situation described above. Configuration 3 allows recording of a flat reference baseline. A change from Configuration 3 to Configuration 1 allows the start of the transient dissipative phenomenon to be precisely controlled.

The Applicants determined that the CDP pulses record genuine output of living systems, by ruling out artifacts as sources. Recordings taken continuously with Configuration 1 (TABLE 1), and no subject, for over 12 hours produced a flat trace with no pulses. Surface zeta potentials were ruled out as the source because a direct short across either the inside or outside surfaces of the large electrode plates produced at contact a single, very low amplitude (<0.5 micro-amp) pulse of about 0.25 sec. duration, with no dissipative pulses. Inductive effects from the organism were ruled out by trying hand contact with only the opposite sides of the resistor, producing at contact a single very low amplitude (<0.5 micro-amp) pulse with no dissipative effect or current flow seen. clothing placed across the electrodes produced no effect, ruling out electrostatic effects from clothing.

When a dielectric (20-micrometer thick polyethylene film) was placed between the hands and the outer surface of the electrodes, a flat line trace with no pulses resulted, as it did when the one or both hands were encased in latex surgical gloves.

Reduction in the area of hand contact with the electrode plate reduces the Pa roughly proportionally. Covering the inside surface of the electrode plates (the side opposite the hand) with polyethylene film had no effect on the Pa value, indicating that the CDP pulses are organized and distributed within the metal matrix of the charge collector plates. Minor variations in hand contact pressure on the electrode plates or muscle twitches in the fingers, if detected at all, were observed as very minor spikes (<0.06 microamps) in the dissipative curve.

Finally, from a record of over 5,000 trace recordings, no trace made on a living organism has ever recorded the absence of CDP pulses.

All of these observations point to the conclusion that these CDP pulses constitute a ubiquitous energy pattern common to living organisms. The fact that plants also produce these signals suggests—the existence of non-living models notwithstanding,—that the device is measuring a ubiquitous biofield.

BRIEF DESCRIPTION OF THE DRAWINGS

The present invention can best be understood in connection with the accompanying drawings, in which:

FIG. 2A shows a basipetal (bottom) end of a plant stem on an exterior surface of a cathode plate electrode and shows an acropetal (top) end of the stem on an exterior surface of an anode plate electrode, and where FIG. 2B shows the reverse, i.e. a basipetal end on an anode and an acropetal end on a cathode;

FIGS. 12A–12G show Charge Density Pulse (CDP) readings of a human subject discussed in Example 5 herein, using the flat plate embodiment shown in FIG. 3A, in connection with chiropractic manipulation treatment;

FIG. 16 shows overlaid Charge Density Pulse (CDP) readings of human subjects with spinal injuries, as discussed in Example 9 herein, also using the flat plate embodiment shown in FIG. 3A; and, FIGS. 17A, 17B and 17C show Charge Density Pulse (CDP) readings of a human subject with a traumatic foot injury as discussed in Example 10 herein, wherein FIG. 17A shows the use of both a flat plate electrode of FIG. 3A in combination with a cylindrical rod electrode shown in FIG. 4, and FIGS. 17B and 17C show Charge Density Pulse (CDP) readings in connection therewith.

DETAILED DESCRIPTION OF SPECIFIC EMBODIMENTS OF THE PRESENT INVENTION

Figure 1:
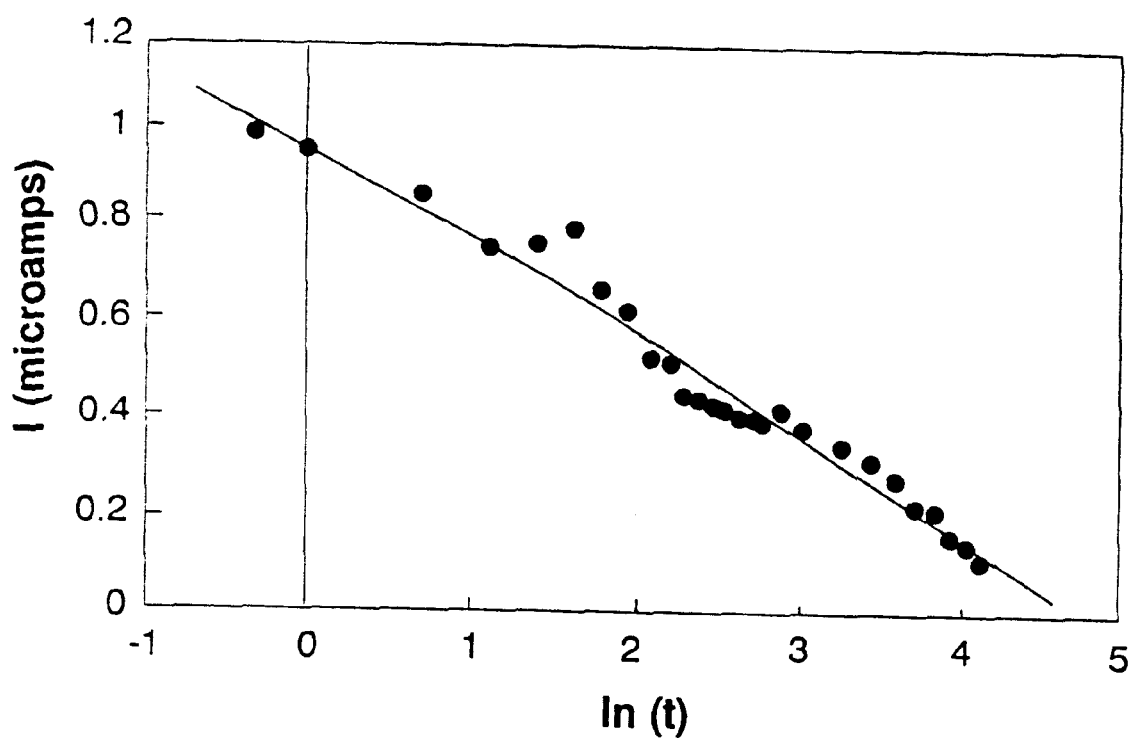
FIG. 1 is a chart of a linear regression analysis of log-time relationship with dissipation of amplitude of current pulses, as taken from a human hand trace.

The present invention is best explained with reference to the following analysis of dissipative curves produced by exposing electrodes to living tissue, to quantify Charge Density Pulse (CDP) pulses as trace recordings.

Analysis of Dissipative Curves

The bioelectric pulse signals emitted by living tissue can be quantified by measuring the peak pulse amplitudes generated over time.

Figure 3A:
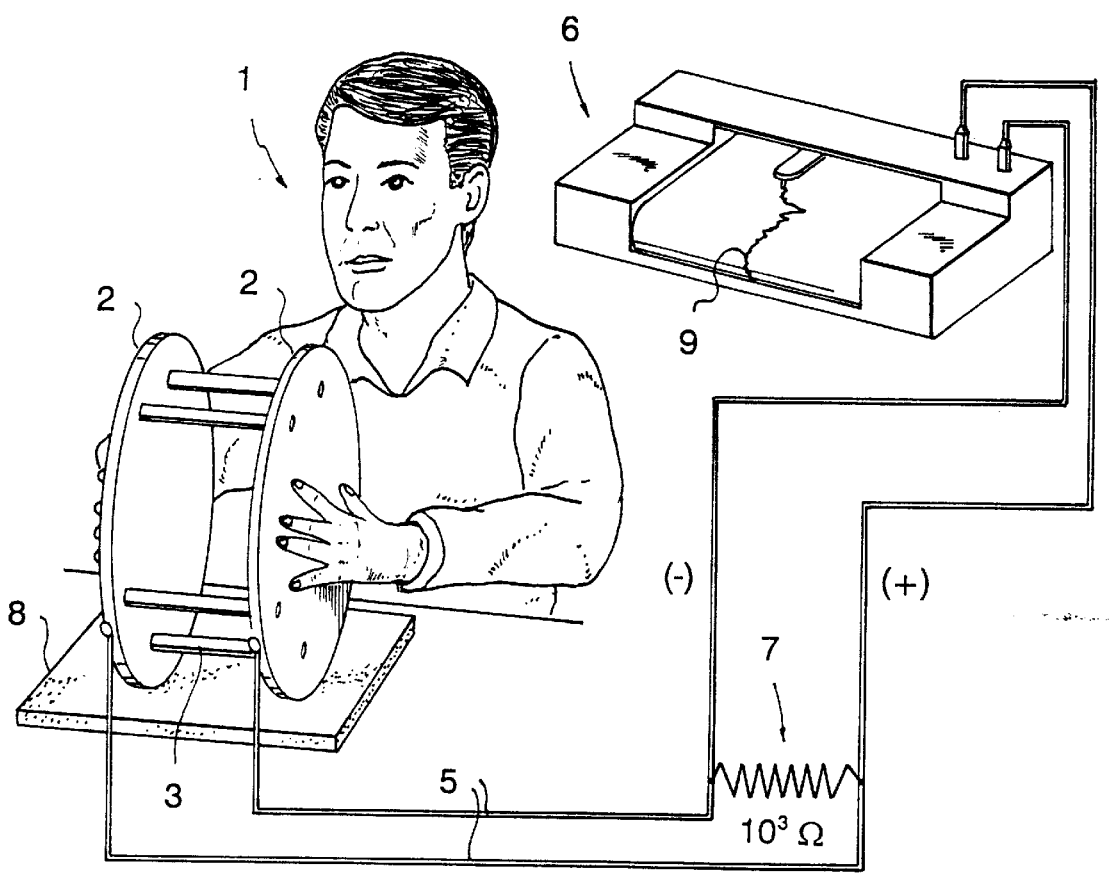
FIG. 3A is a front perspective view of a human subject using the CDP apparatus with one embodiment of a configuration of the present invention.
Figure 3B:
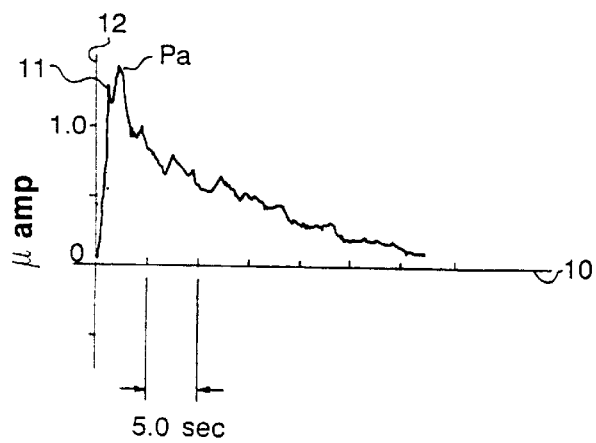
FIG. 3B is a chart of a typical CDP pulse trace on plates with human hands.

After reaching peak pulse amplitude (Pa) the envelope of the Charge Density Pulse (CDP) curve decreases non-linearly toward the base line of the trace. From analysis of this dissipative phase of the hand traces, one finds a log time relationship, a typical example of which is shown in the FIG. 1 regression curve (r=0.98), the general form of which is given by, $$I = -a_1[ln(t)] + a_2 \qquad (1)$$

where I is the current level at t seconds into the trace, and $a_1$ and $a_2$ are constants. This relationship is suggestive of an unstable system in which the current density exhibits a systematic decrease with time. Here one lets the rate of charge carrier dissipation at the electrodes be a function (indicated by "f") of Pa, t, and u as follows, $$-dI/dt = f(Pa, t, u) \qquad (2)$$

where Pa is the maximum charge carrier concentration at the inflection point in the CDP trace, and u their ionic mobility. As a first approximation the current is taken as inversely proportional to time, since the level of charge carriers decreases after the initial Pa level. From this one sets up the rate function, $$dI/dt = -(Pa\ u)(1/t) \qquad (3)$$

and $$\int dI = -(Pa\ u)f(1/t)dt \qquad (4)$$

where $\int$ represents the mathematical integral sign, and which after integrating gives, $$I = -(Pa\ u)(ln\ t) + k \qquad (5)$$

since Pa and u are taken as constants for any given trace, this rate function is identical in form with equation (1), obtained from empirical data such as shown in FIG. 3B.

The same type of dissipative function is characteristic of traces taken from living plant material. The CDP traces in FIG. 2 were obtained from a freshly excised, red flowered Impatiens spp. stem about 30 cm long and less than 1 cm diameter placed across the outside surfaces of the large aluminum electrode plates. In the A-trace the basipetal end of the stem was positioned on the cathode and in the B-trace on the anode. As in the hand traces, a distinct polarity effect was consistently observed in living stems as well as in intact, living plants. Species tested include *Pelargonium maculatum*, Impatiens spp., Begonia spp., *Glycine max*, and *Zea mays*.

To record CDP responses, in the embodiment shown in FIG. 3A, the CDP response traces are generated by placing the palms of the hands on the outside surface of vertically positioned aluminum plates where, as depicted in FIG. 3A, the test subject 1 is shown sitting comfortably in front of the apparatus. These preferably circular, semi-polished charge collector plates 2 are preferably about 31 cm diameter, about 0.6 cm thick and are preferably separated by nylon spacers 3, (such as four spacers), which provide an 8 cm air gap. The plates 2 can also be other conductive metals, such as copper, brass, stainless steel or alloys thereof or conductive-non-metallic materials, such as conductive polymers. Connectors 4 at the edge of the plates 2 extend into the metal, through the oxidized surface.

As also shown in FIG. 3A, wire leads 5 extend from these connectors to a data recorder 6, in this case a chart recorder with maximum 1 mV full scale input sensitivity and 2 Hz minimum frequency response.

Any current fluctuations were detected by placing a 1.0 K ohm resistor 7 across these leads and recording the pulses on the chart recorder. The electrode plates should be placed upon a dielectric insulating pad 8.

With most subjects the sensitivity of data recorder 6 is set at 10 mv full scale. From Ohm's law it can be seen that the chart recorder scale gives a direct measure of the current flow in microamps, that is, a 1.0 mv change across the resistor is equivalent to a 1.0 microamp current flow through the system. In place of a chart recorder a computer has been used with a signal amplifier and analog/digital converter card, thus allowing detailed analysis of the microstructure of the traces using a standard mathematical software program (such as DataLab Solutions by Lab Tech).

As also shown in FIG. 3A, the most important aspect of these recordings is the presence of large fluctuations or pulses of charge transfer through conductive plates 2, labeled as Charge Density Pulses, (CDP) 9. The temporally decreasing amplitude of these pulses suggests a dissipative system, with fine structure oscillations persisting throughout from 0.5 to 1.0 minute duration test intervals, during which the envelope of the pulses decreases non-linearly toward the baseline according to a log-time relationship which is typical of dissipative systems.

The circuitry shown in FIG. 3A is arbitrarily organized so that the left palm contacts the designated cathode plate 2 and the right palm the anode plate 2, as determined by the input of their respective leads 5,5 into the chart recorder 6. This generally produces CDP curves which after 10–15 seconds diminish to much lower amplitudes and approaches the zero or base level (as in FIG. 3B).

Figure 2:
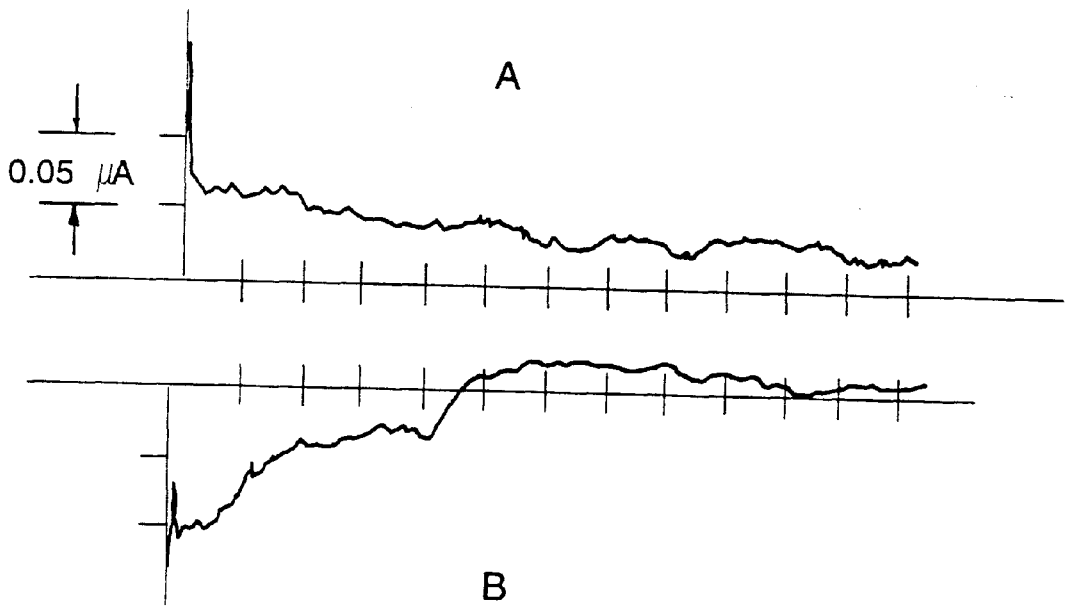
FIG. 2 is a mirror image chart of Charge Density Pulse (CDP) traces in plant stems from living Impatiens plant stem, where

If, however, the palms positions or lead wires were reversed, the CDP curve has essentially the same shape but is peaked in the opposite direction relative to the base level, constituting a "mirror image" as also shown analogously in the plant system shown in FIG. 2. Thus the system of the present invention measures polarity differences between the palms of the hands.

In the majority of cases, the distribution of charges on the surface of the hand is primarily cathodic on the left and anodic on the right, though under certain conditions the polarity can change. This basic hand polarity has been observed, irrespective of the chirality of the subject, in the over fifty (50) subjects studied, but the amplitude of the pulses and their fine structure vary considerably between test subjects.

A typical CDP hand trace is shown in FIG. 3B for a 30 second test interval. These chart data were analyzed by recording the peak amplitude at the point on the curve where the current begins to drop back to the base line level 10. This inflection point, designated as Pa, occurs well after any initial contact potential changes 11, usually around 5–10 sec. into the trace. The value of Pa as given here is in microamps 12. The maximum current density, Id (microamps/sq.cm.) in the tissue contact region is given by:

$$Id=P_a/a \tag{6}$$

where a is the area of tissue contact. In adult humans the hand contact area is in the range of 90–110 sq.cm., in plant stems the contact area is in the range of 0.3 to 0.8 sq.cm.

This peak amplitude analysis provides information from one time point on the 60 sec. response curve. The exact form of the oscillating pulses can be analyzed both macroscopically and microscopically by a variety of computer-based techniques, using data from an appropriate analog-digital converter input system.

Figure 4:
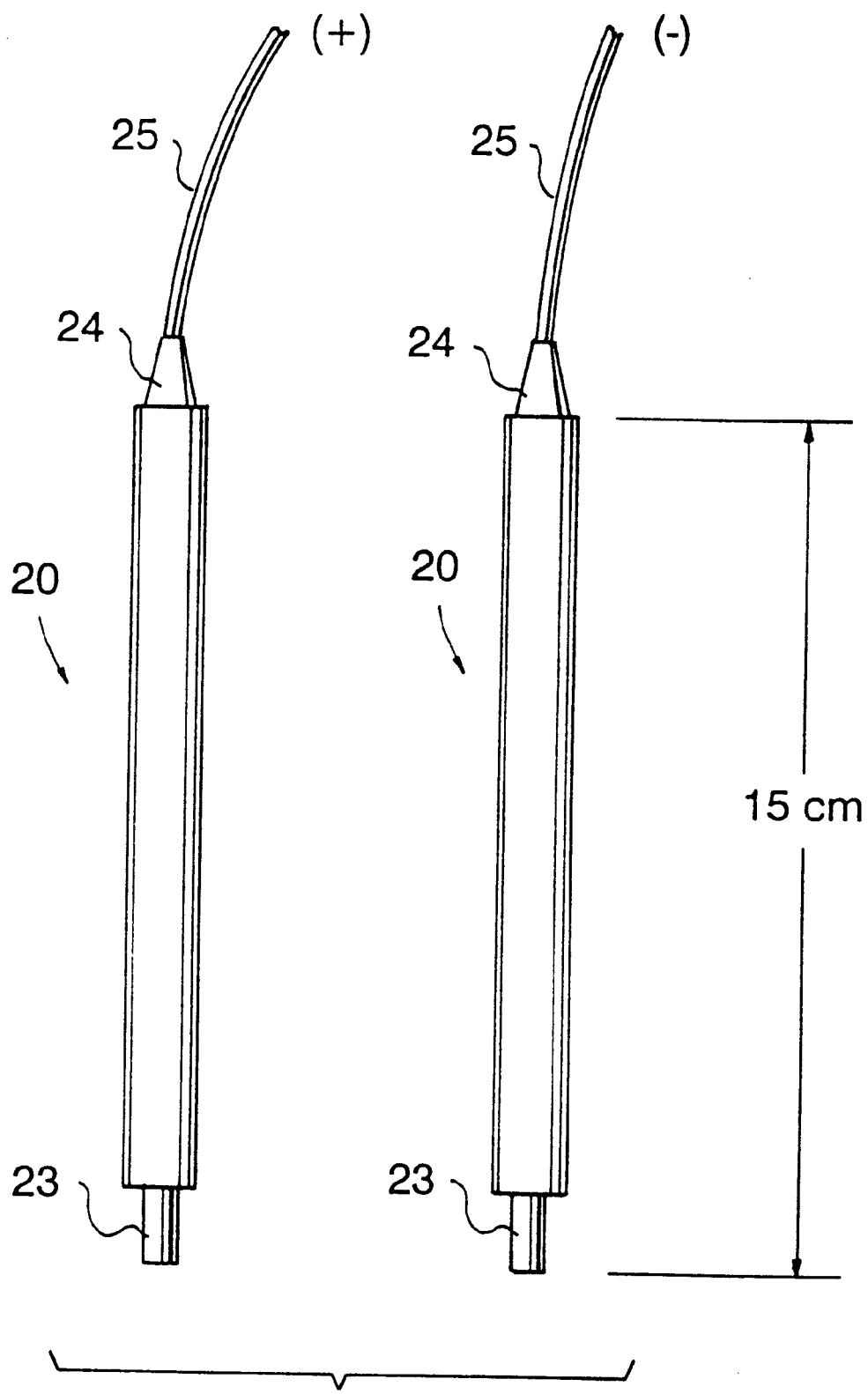
FIG. 4 is a front elevational view of an alternate embodiment for cylindrical rod CDP electrode probes.

Another form of the electrode system shown in FIG. 4 includes cylindrical rod electrodes 20 of solid aluminum or other conductive metals, i.e. copper, brass, stainless steel or other alloys or combinations thereof, or conductive non-metallic materials, such as conductive polymers. Cylindrical rod electrodes 20 are-semi-polished on one flat end 23, with lead wires 25 soldered onto the opposite end 24 and connected across a 1.0 Kohm resistor (not shown) and to a 1.0 millivolt chart recorder (not shown) in the same fashion as described previously in FIG. 3A with respect to the large, plate-shape electrode plates 2 being connected across a 1.0 kilo-ohm resistor 7 to a data recorder 6 therein.

In the embodiment shown in FIG. 4 one electrode 20 is held stationary on a reference point on the body while the other electrode 20 can be moved to contact other parts of the body to produce CDP pulse traces representative of specific areas. Applicant's studies reveal that this has produced in one case a lowered CDP Pa value when the movable electrode contacted an injured ankle. The Pa value increased over time as the ankle healed.

Figure 5:
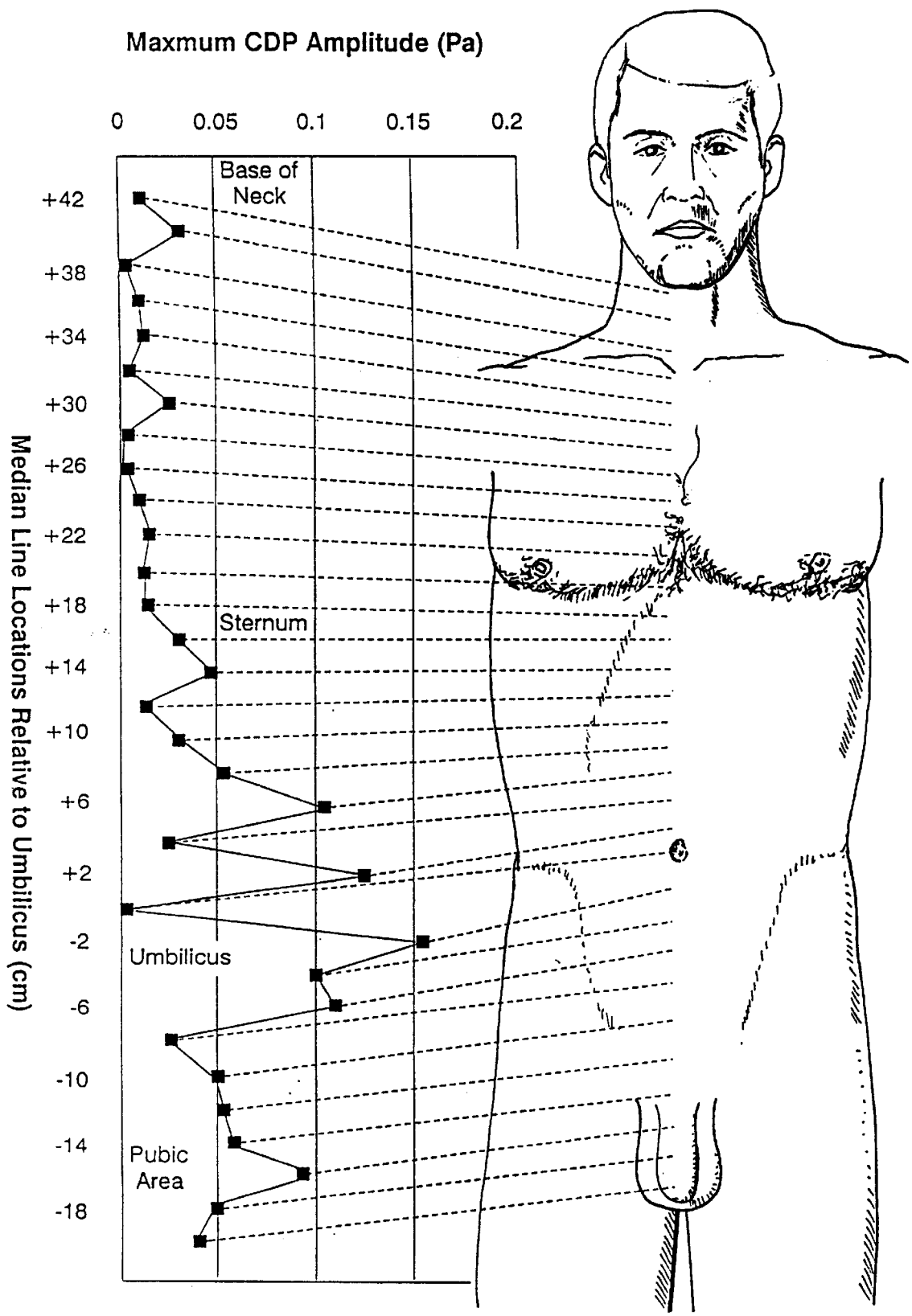
FIG. 5 is a chart of Pa, primary pulse current amplitude, at various points on the mid line of the human torso, showing the human torso in front elevational view.
Figure 5A:
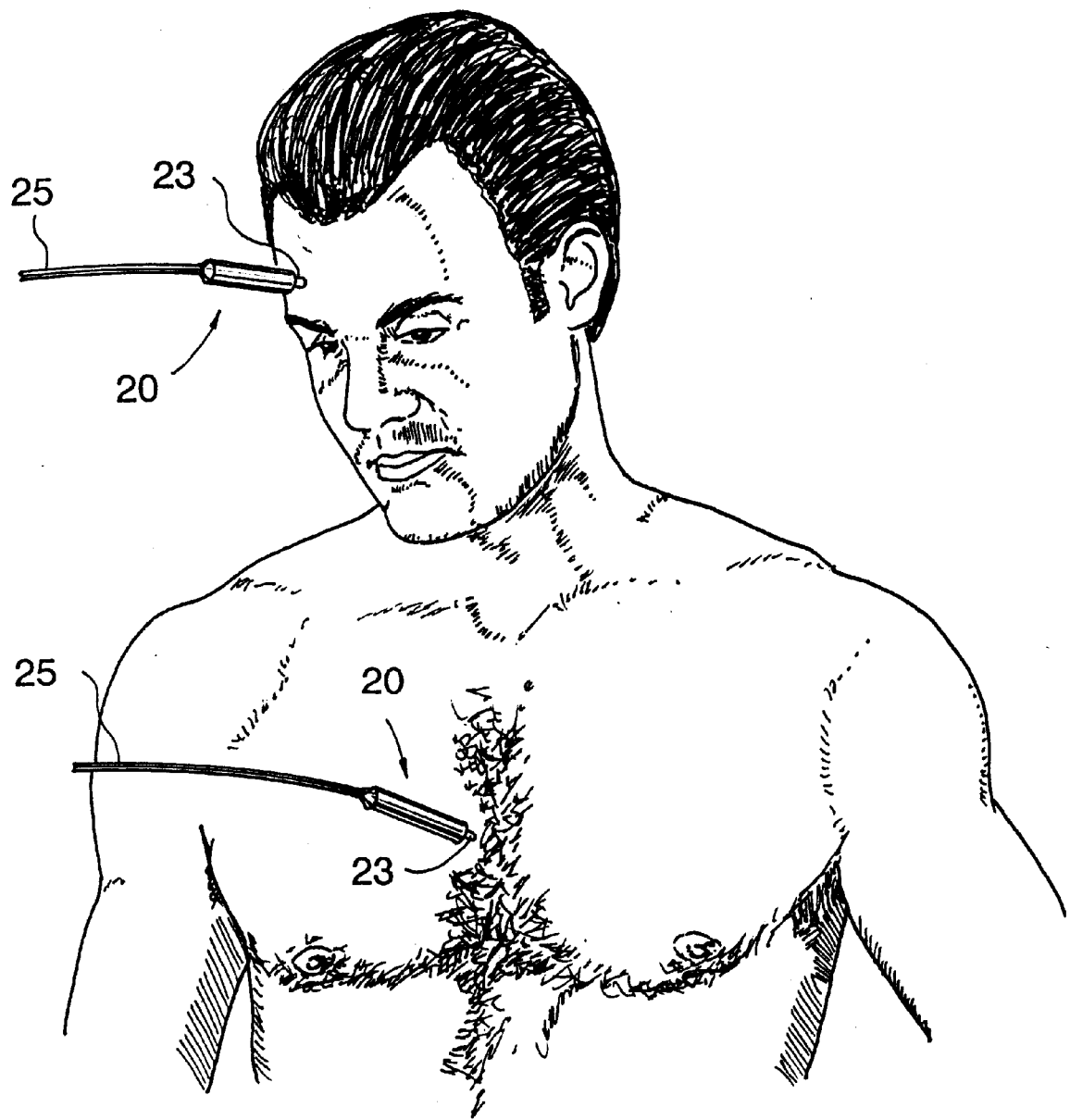
FIG. 5A is a close up detail view of an alternate embodiment for electrode placement upon the body of a human subject.
Figure 6:
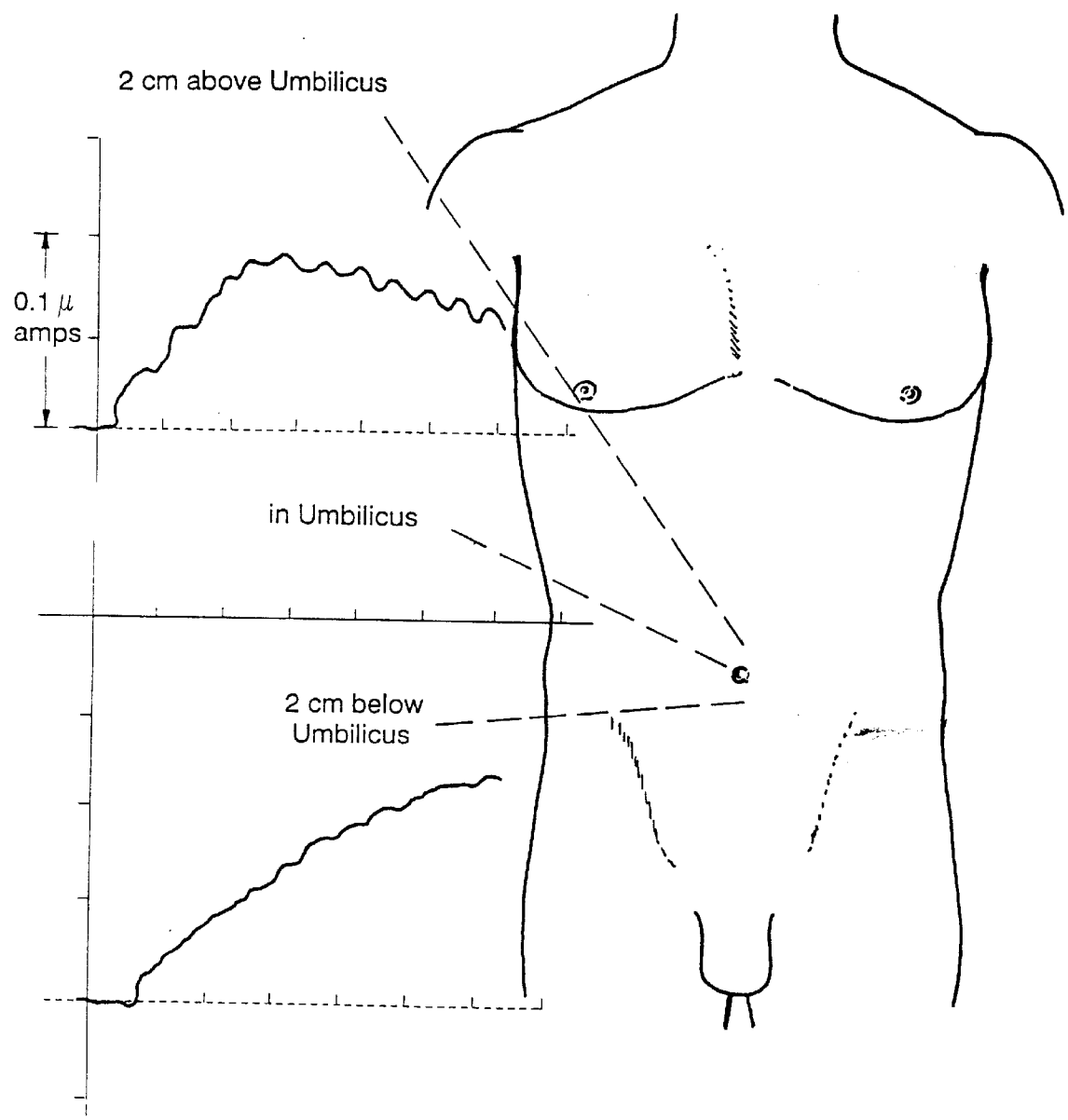
FIG. 6 is a chart of differing CDP traces taken just above and below the human umbilicus, showing the human torso in front elevational view.

A systematic survey of the centerline of the human torso has shown a pattern of Pa value similar to the map of the so-called chakra energy sites in the human body, as shown in FIG. 5, FIG. 5A shows an alternate embodiment where one cylindrical electrode 20 was placed in the center of the forehead as a reference electrode and the other cylindrical electrode 20 moved to contact the skin at points 2 cm apart down the midline of the human torso. Markedly different CDP pulse patterns occur within 2 cm on either side of the umbilicus, as shown in FIG. 6, where values are that of the Pa amplitude. This kind of monitoring is useful in energy disciplines, which concentrate on altering the strength of energy in particular chakras. The CDP pulse patterns produced with this system are similar in all general respects—except, amplitude—to those produced with hands applied to the large electrode plates 2, as in FIG. 3A.

EXAMPLES

Investigations have shown links between these CDP pulse phenomena and various internal biological activities. Several experiments show that the energy being measured by the present invention is at least partly generated by known electrochemical, physiological processes such as ion mobility and enzyme activity. Other examples show the effectiveness of the present invention in evaluating pain, injury, and the effectiveness of certain types of therapies.

Example 1

Linkage with Cell Membrane Porosity: Addressing the question of how and where the CDP pulses originate within the living system can be done with utilization of perturbation kinetics, which is most easily carried out in plant material.

The influence of known quantities of microwave energy on the CDP pulses originating in 5 cm long stem sections from living Impatiens plants was examined using small, cylindrical aluminum electrodes 12 cm long and 0.64 cm diameter with flat semi-polished tissue-contacting ends.

These electrode probes were horizontally mounted on a lab bench covered with polyethylene film. The ends of freshly-excised plant sections were placed with the basipetal end contacting the cathode and the acropetal end the anode end. With this orientation the mean base line Pa level was determined from 8 non-exposed sections to be 0.40±0.08 microamps.

During microwave exposure the stem sections were placed horizontally in a microwave oven which was determined calorimetrically to have an energy output of 0.107 J/sq.cm./sec. After exposure to the microwaves each sample was allowed to reach room temperature before measuring the CDP pattern.

Pa levels increased significantly with increasing microwave exposure. Though microwave radiation is non-ionizing, the thermal energy disrupts tissue and decreases cell membrane integrity. Analysis suggests that the increase in Pa levels with exposure time is the result of cell membrane damage. If this damage is represented by a random target model then in a population of microwave exposed cells the Pa alterations can be examined with the Gompertz Function utilized in radiation biophysics to describe the relationship between cell damage and exposure time. As applied here this function is given as, $$ln(Pa)=k(t)+b \tag{7}$$

where t is the exposure time (sec.), k the rate constant, and b the intercept constant.

Figure 7:
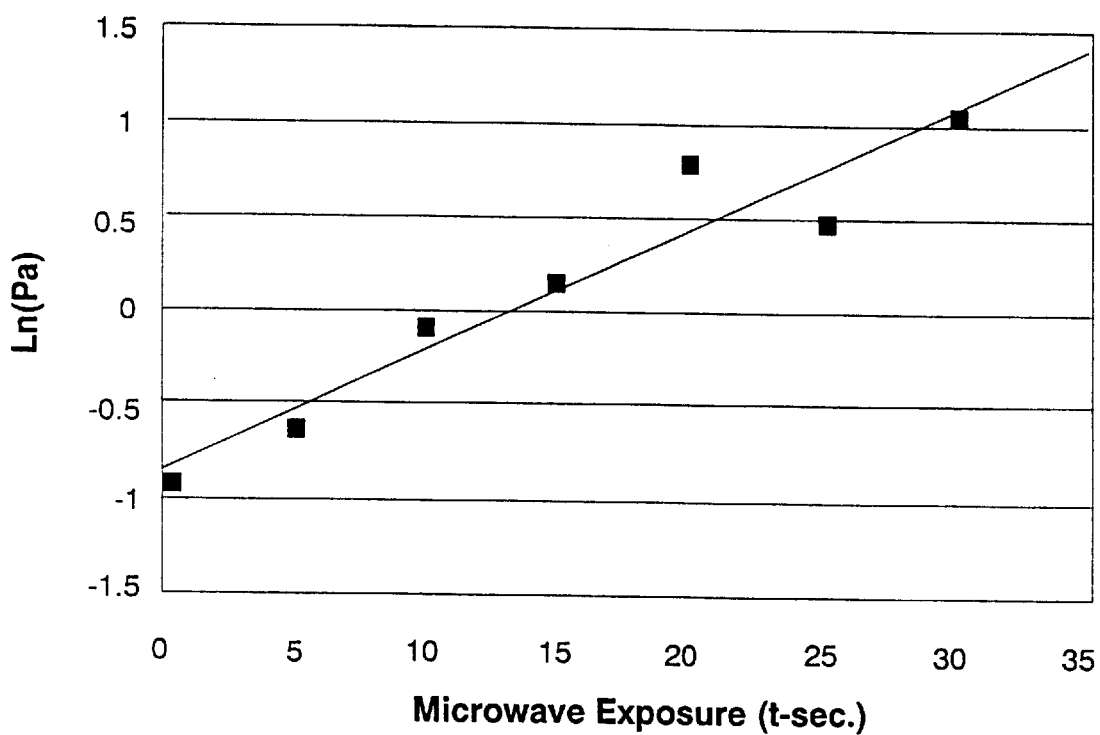
FIG. 7 is a chart of increasing pulse strength (Ln (Pa)) from a CDP trace of a plant exposed to microwaves vs. time of exposure.

The Pa levels obtained from microwave exposed stem sections are plotted in FIG. 7 according to equation (7). The high degree of correlation (r=0.96) clearly suggests that the damage is occurring at the cellular level. Thus with increasing microwave exposure a cell's membrane porosity increases, allowing ions and other materials to leak through and producing higher amplitude, oscillatory CDP structures transmitted through the tissue. This is clear evidence that cell membrane porosity is an important factor involved in the dissipative phase of the CDP traces.

Finally, the maximum Pa levels are observed to lie in the 1 to 10 microamps region, a range consistent with bioelectric currents developed during normal membrane transport processes in living systems. Since the basic CDP patterns, Pa levels, and in both plant and animal tissues, responses to external perturbations and polarity differences, are similar, it can be assumed that these results in plants extend to animal subjects as well.

Example 2

Reaction-Diffusion Patterns: One can obtain some idea of the transport properties by examining the effect of reaction product formation at the electrode contact sites. With rapidly repeated hand traces one can detect a change in the Pa level due to feedback inhibition consistent with a buildup of reaction products in the epidermal tissue.

Figure 8:
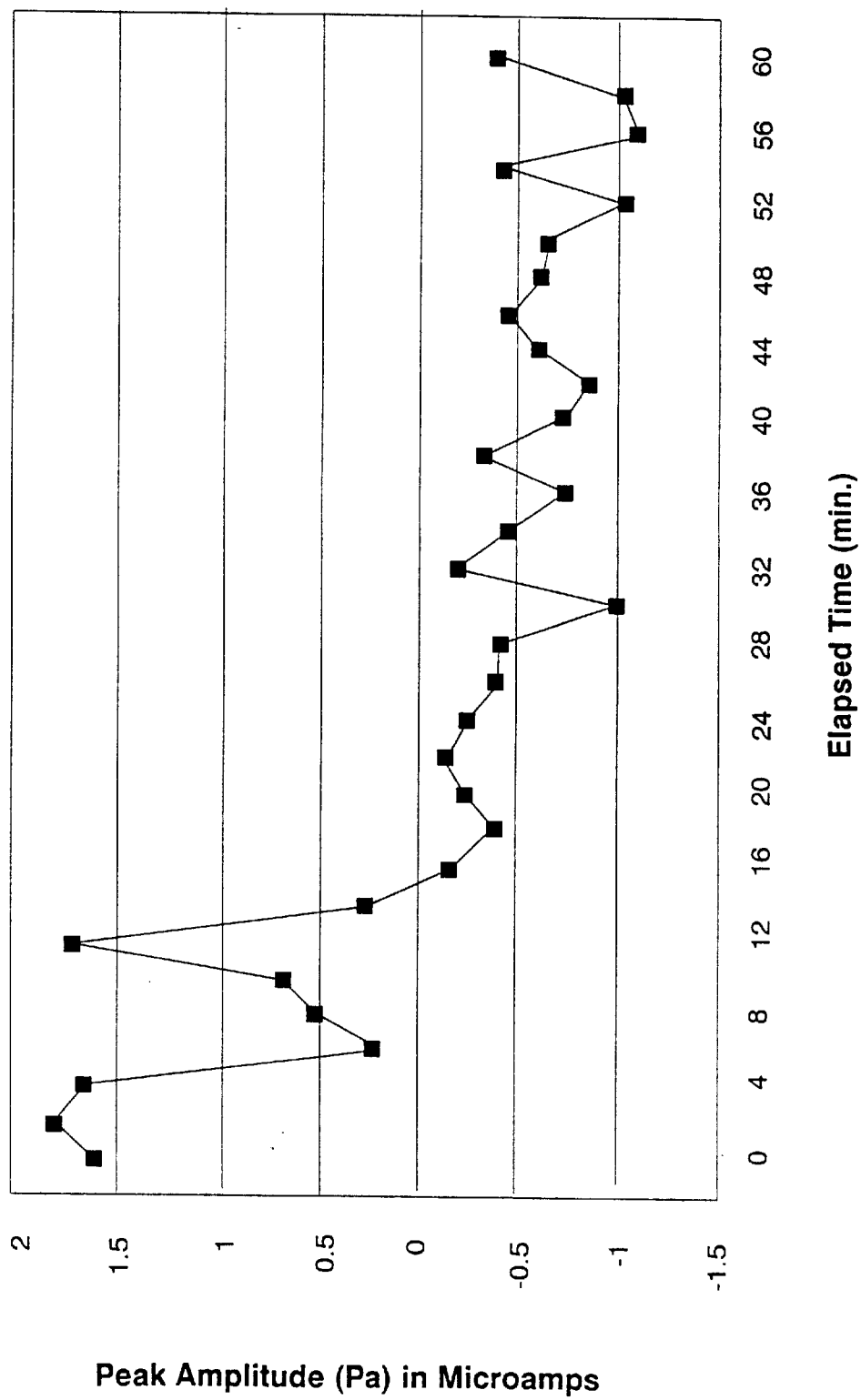
FIG. 8 is a chart of CDP traces taken at 2 minutes intervals.

The results in FIG. 8 are from a 60 minutes test during which CDP traces were taken every 2 minutes. At the onset of this test (0–15 min.), the rapidly changing Pa levels are characteristic of spatio-temporal, self-organized reactions far from equilibrium and taking place at solid surfaces (ref.: G. Ertl, "Oscillatory kinetics and spatio-temporal self-organization in reactions at solid surfaces", *Science*, 254, (1991) pp.1750–1755). About 16 minutes into the test the Pa values became negative and continued with this polarity reversal until the end of the test period, a clear indication of the buildup of reaction products forming a local reservoir of charges with an opposite sign to those originally present. This reaction product buildup seems to have a short refractory period. If the between-test interval is increased from 2 to 5 minutes or more the rapid decline in Pa (as in FIG. 8) does not take place.

Example 3

Evidence for Electrochemical Involvement: It is quite apparent from the consistent form of the dissipation function discussed above that the kinetics involved in producing CDP pulses in the metal matrix of the electrodes is not a random process. If this is connected to electrochemical processes then one would expect the rate constant k to be dependent on temperature according to the Arrhenius Equation:

$$K=A[\exp.(-E/RT)] \qquad (8)$$

where E is the Gibbs free energy of activation, R is the Boltzman constant, T the absolute temperature, and k is the reaction rate constant, which in a CDP trace is equivalent to the dissipation constant in the equation. To examine the electron reaction dynamics within the matrix of the aluminum electrodes, data was plotted from routine hand traces taken at the same period of day over two months, with differing ambient temperatures of the metal electrodes, ranging from 21° C. to 27° C. Six data points were taken from each individual CDP trace, starting at the Pa level (normalized at 5 seconds into the trace) and continuing every 5 seconds thereafter. For each CDP trace the current level was examined as a function of log (t) and the value of k determined from linear regression analysis. The consistent form of the CDP dissipation function (as in Equation (1)) was evident from the fact that the R squared value for 35 I-log(t) curves were all in the range from 0.9 to 0.99.

Figure 9:
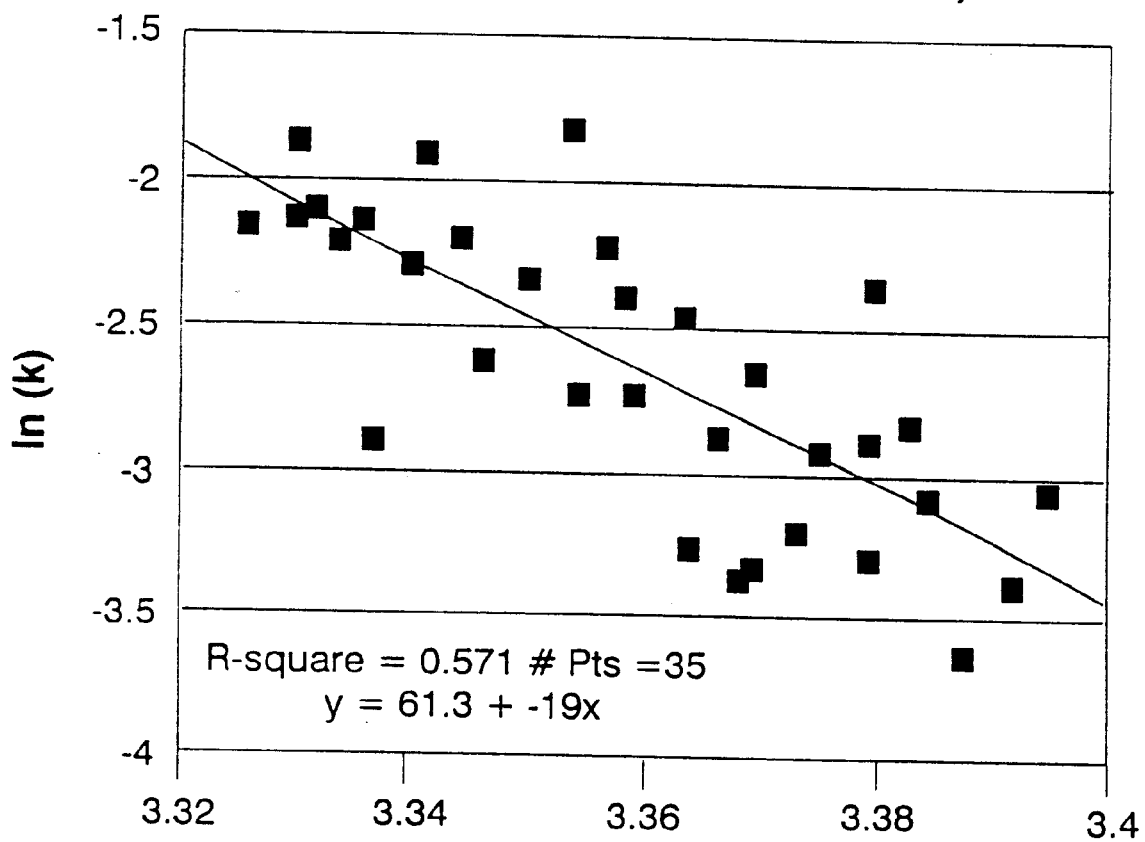
FIG. 9 is an Arrhenius plot of ambient temperature influences on rate constants (k) from hand traces.

FIG. 9 shows the Arrhenius plot of these 35 CDP traces (r=0.76) and from the slope a value was obtained for E of 37.8 k cal./mole The activation energies of most chemical reactions lies in the range 20–40 k cal/mole, therefore the E for the CDP pulse activation is well within the range of electrochemically activated complexes.

Example 4

Enzyme Activity: The involvement of enzyme kinetics in the production of CDP pulses are suggested by examining the CDP traces from heated carrot roots and applying the Arrhenius activation energy model.

Sections of living carrot root 4 cm long were excised from the apical end, wrapped in plastic and sealed in a plastic bag, all of which was then lowered into a temperature-controlled water bath and allowed to reach temperature equilibrium (approximately 30 minutes). After removal from the water a CDP trace was taken along the root's center line by placing 6 mm diameter aluminum electrode probes in the zone of primary xylem (with the cathodic electrode contacting the basipetal end of the sample carrot section.)

From each CDP-temperature trace the rate constant k was determined from linear regression analysis applied to time-normalized data plotted, as shown in FIG. 1.

Figure 10:
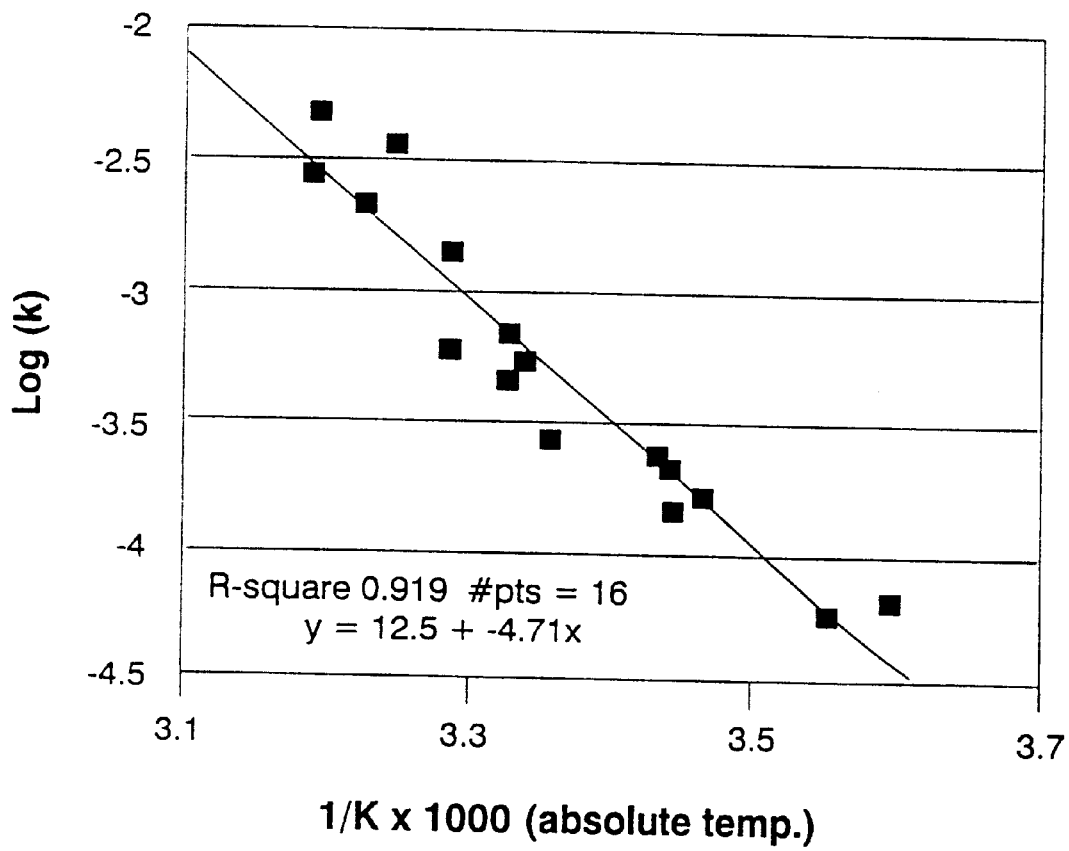
FIG. 10 is a chart of an Arrhenius plot of CDP rate constants (k) in carrot plant tissues.

A total of 16 tests conducted over a temperature range of 5° C. to 39° C. are plotted in FIG. 10 according to equation (8), and the high correlation coefficient of r=0.96 indicates that temperature activated reactions are involved and from the slope there was obtained an activation energy of 9.4 k cal/mole.

In his book "Bioenergetics" (1957) Szent-Gyorgyi addressed the problem "How does energy drive life?" (page 3). He focused on the questions raised by the problem of how the energy of the high energy phosphate bond, $^-P$, in the ubiquitous Adenosine Triphosphate (ATP) molecule is utilized in living systems. He started by making a distinction between bond energies and excitation energies. Bond energies are enclosed within molecules and have no outward action; this fact is represented by the symbol (E). Excitation energies are mobile and may interact with their surroundings; this fact is represented by the symbol E*. So the problem "how does energy drive life?" may be expressed by asking a question of the form: "Is the (E) of ATP exchanged for E* in the situation to be understood?" (page 8). In the present context this means asking: "Can the generation of biofield energy, as detected by the CDP device, be understood as an exchange of the (E) of ATP for E* ?".

Later in his book (page 24) Szent-Gyorgyi refers to the energy of $^-P$ as "the biological energy unit", with a value of the order of (in modern notation) 10.0 k cal/mole (compared with 9.4 k cal/mole in the CDP activation energy). He goes on to point out that a photon of this energy has a wavelength of $2-3\mu$, corresponding to the near infrared.

More recently Harold (1986) in his book "The Vital Force: A Study of Bioenergetics" refers to "the proton-translocating ATPase" in the context of a discussion of the Chemiosmotic Theory of energy coupling by ion currents. He writes (page 68) "the proton-translocating ATPase is known to generate a $\Delta$ p on the order of . . . 4.6 kcal/mole. Since the free energy of ATP hydrolysis in the cytoplasm is about 10.0 kcal/mole, the data are consistent with the transport of at least two protons per cycle."

If one takes Harold's quoted value of 4.6 kcal/mole for the proton-translocating ATPase, the corresponding number for two protons is 9.2 kcal/mole. The experimentally determined number of 9.4 kcal/mole reported above for heated carrot root is within 2.2% of this figure. This result strongly suggests that the generation of biofield energy, as detected by the CDP device, can be understood as an exchange of the bond energy (E) of ATP for the excitation energy E* and, consequently, that the CDP device may have considerable potential as a tool for the study of Szent-Gyorgyi's problem "How does energy drive life?" by providing access to quantitative aspects of fundamental bioenergetic processes in intact living systems.

An additional factor providing strong support for enzymatic involvement in the CDP oscillatory process is the fact that the rate constant k drops very sharply as the tissue temperature reaches 40° C.

Figure 11:
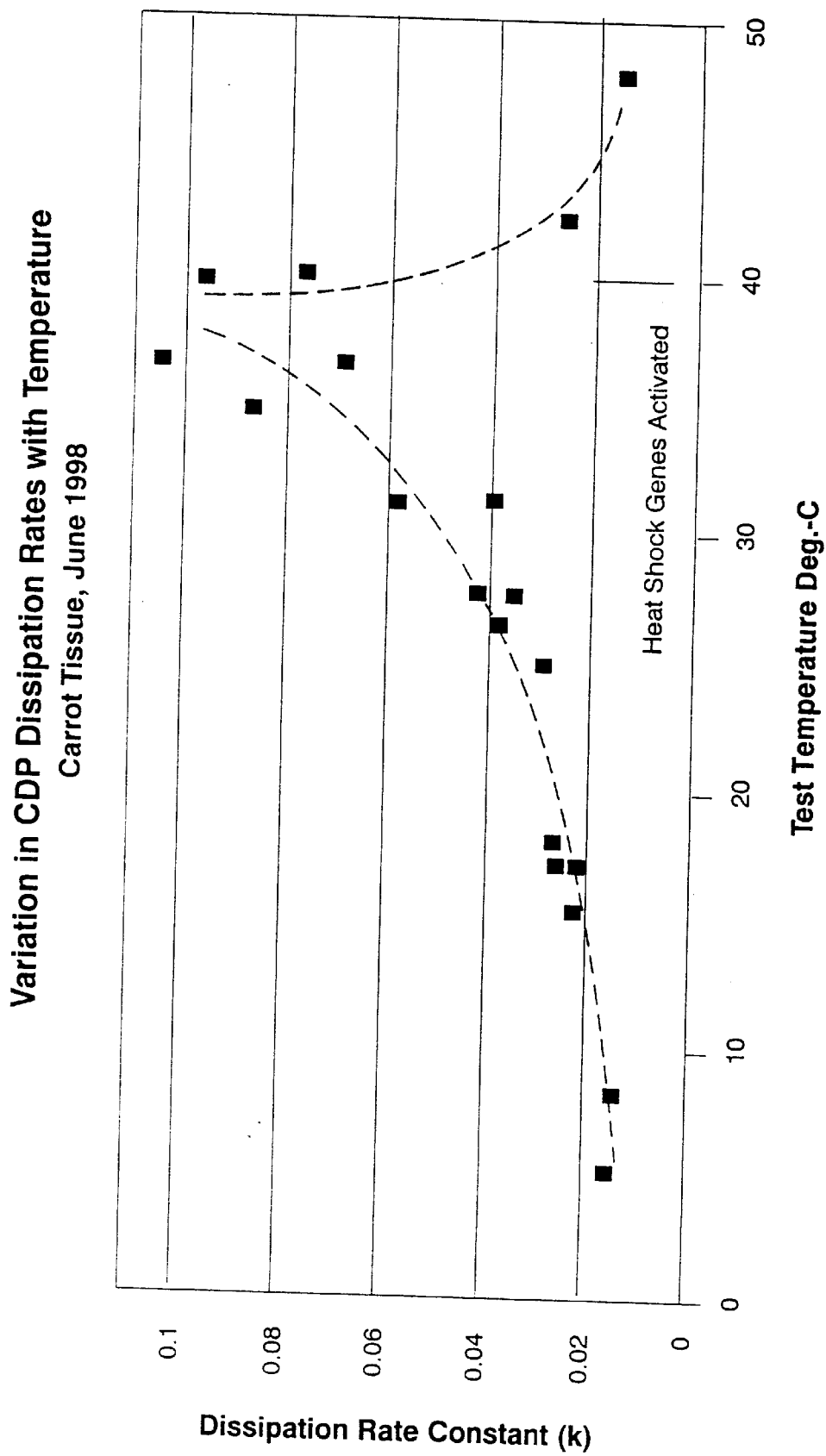
FIG. 11 is a chart of activation of plant heat shock genes as indicated by change of CDP dissipation rate constant around 40° C.

FIG. 11 shows k values obtained from individual tests conducted below and above the critical 40° point. It is well known that at approximately 40° C. heat shock genes are activated. At this temperature most of the normal functioning enzymatic systems are deactivated and remain so for several hours after the temperature is reduced below this critical point.

In the heat shock zone secondary alterations are produced in the enzymatic reactants and the Arrhenius reaction rate model is no longer applicable. This further links the CDP pulses to normal metabolic processes in biological organisms.

Example 5

Chiropractic treatment is designed to relieve pain and adjust imbalances in the spine, which may impinge upon nerve function. Lack of an objective criterion for effectiveness has plagued this discipline when trying to qualify for reimbursement with health insurers, as well as in trying to obtain acceptance in the scientific community.

The present invention therefore provided a consistent, objective means by which to measure such effectiveness. In this example, a human subject placed their palms and fingers on the aluminum electrode plates connected to a resistor and chart recorder, as described previously in FIG. 3A. Electric biofield pulses were recorded for just 30 seconds in the manner described above.

These recordings were tabulated, as shown in FIGS. 12A–12G, which show,the CDP readings of a subject before and after chiropractic treatments.

Figure 12A:
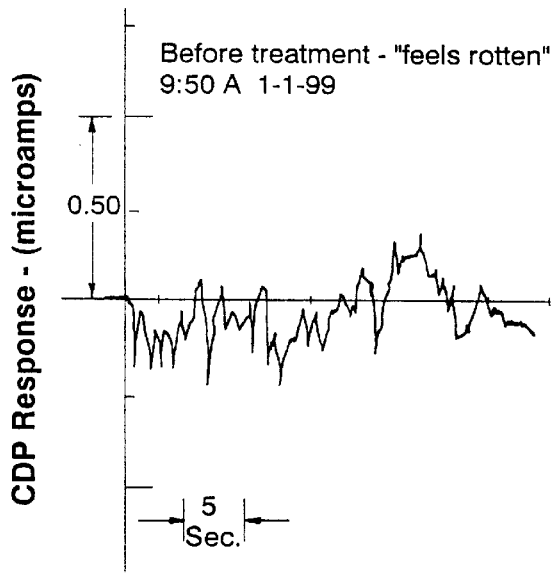

In FIG. 12A, the subject reported feeling bad before the treatment and her pulse trace was typical of an individual in pain, showing tall spikes with many occurring below the baseline in 'negative' values.

Figure 12B:
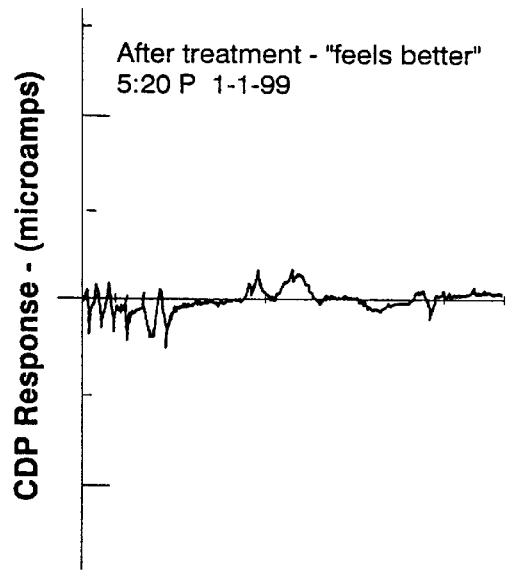

After chiropractic treatment the subject reported feeling much better and her CDP trace recordings in FIG. 12B showed fewer negative values and a pronounced lessening of the amplitude of the spikes.

Figure 12C:
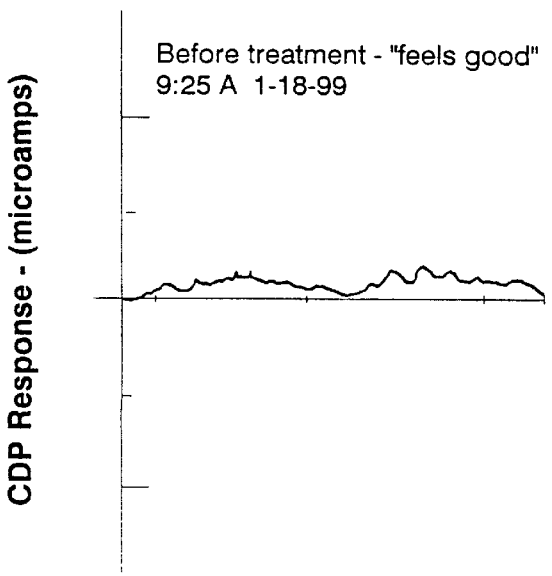

FIG. 12C shows the same subject's trace taken before a treatment at a time when she reported feeling well. There is an absence of large spikes and negative values.

Figure 12D:
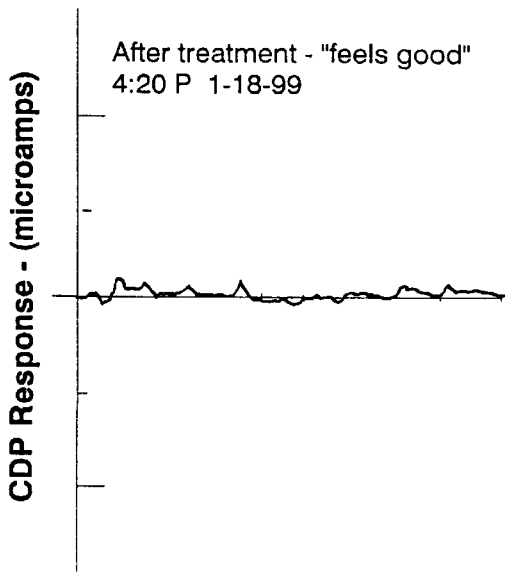

FIG. 12D shows a CDP trace taken immediately after this second treatment and shows little change in the subject.

FIG. 12E shows the subject's CDP trace at 9:35 A.M., before treatment. After treatment the subject's trace was again taken at 4:35 P.M. by which time she reported a headache.

FIG. 12F illustrates this second trace CDP which contained the large spikes and occasional negative values recorded in the patient in FIG. 12A (though not as extreme).

The subject then took a hot bath, reported the headache gone, and recorded the CDP trace in FIG. 12G with no large spikes or negative values. These consistent results indicate that the change in CDP traces is not simply an artifact of the chiropractic treatment but rather a product of effective relief of pain.

Example 6

Treatment of pain by the medical community and others is hampered by lack of an objective way to record pain levels. Subjects vary widely in how they report pain and lawsuits often involve contention over whether the victim of an accident is in fact in severe pain.

Therefore, the present invention provided a method by which pain was objectively assessed simply by having the subject place their palms and fingers on the flat aluminum plates connected to a resistor and chart recorder by lead wires, as shown previously in FIG. 3A, and recording bioelectric pulses in the aforementioned manner for 30 seconds.

Figure 13A:
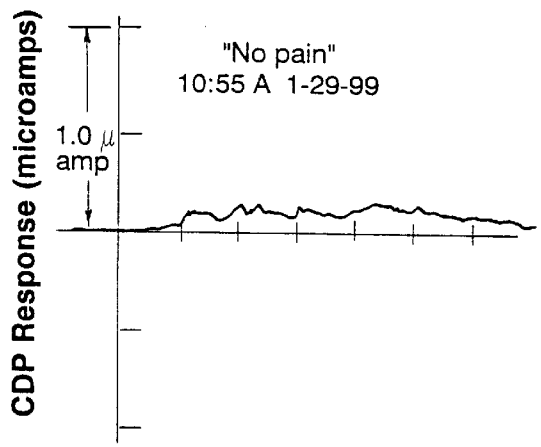
FIGS. 13A–13D show Charge Density Pulse (CDP) readings of a human subject discussed in Example 6 herein, also using the flat plate embodiment shown in FIG. 3A, in connection with pharmaceutical treatment of pain.
Figure 13B:
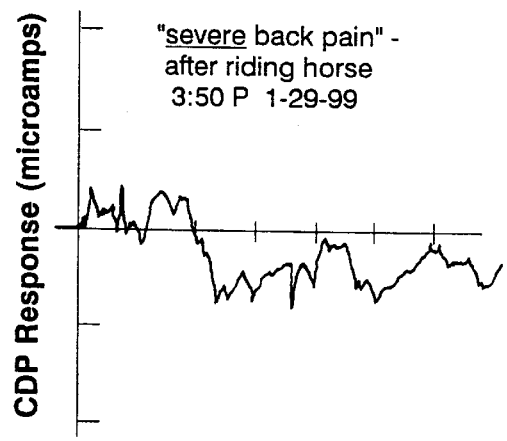

In this Example, FIG. 13A illustrates a morning trace on an individual with no pain, while FIG. 13B shows a trace taken the afternoon of the same day after the subject reported feeling severe back pain after horseback riding. The increase in large spikes and negative readings (below the baseline) is typical of severe pain.

Figure 13C:
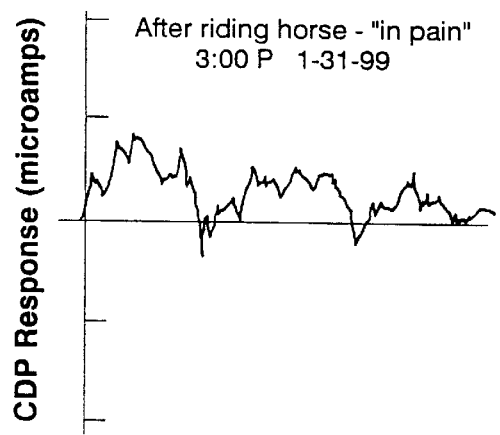

On another day the same subject again reported severe back pain after horseback riding and produced the pulse train in FIG. 13C with large spikes, which occasionally dip below the baseline.

Figure 13D:
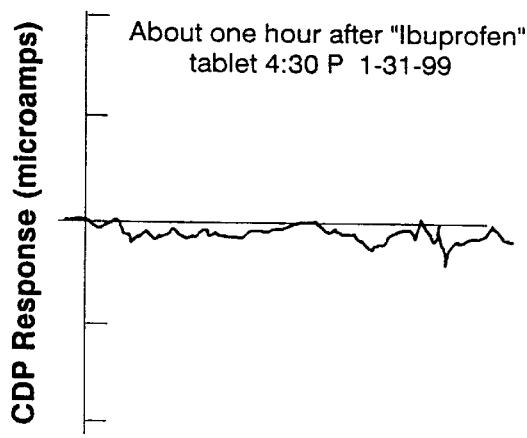

The subject ingested an Ibuprofen tablet 30 minutes later and one hour after the ingestion produced the CDP trace in FIG. 13D. While the CDP trace was found to be mostly below the baseline, the large spikes were gone, indicating a more tolerable level of pain, as well as the effectiveness of the Ibuprofen tablet.

Example 7

Example 7 shows both the ability of the present invention to quantify pain as well as the effectiveness of an alternative therapy, namely a form of hands on healing. The data recordings were done with palms and fingers on flat aluminum electrode plates connected to a resistor and chart recorder as previously described in FIG. 3A herein.

Figure 14A:
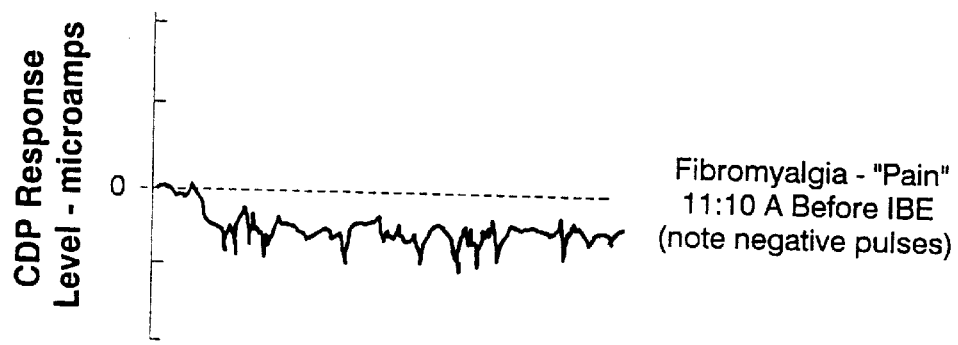
FIGS. 14A–14G show Charge Density Pulse (CDP) readings of a human subject discussed in Example 7 herein, also using the flat plate embodiment shown in FIG. 3A, in connection with "hands on" treatment of fibromyalgia pain.

The subject in this case suffered from the painful condition of fibromyalgia and produced the CDP trace in FIG. 14A at 11:10 A.M., after reporting moderate pain throughout the body. The predominantly negative readings combined with numerous spikes to confirmed the accuracy of the subject's report. Immediately after this CDP trace the subject received a treatment of a type of "hands on" healing.

Figure 14B:
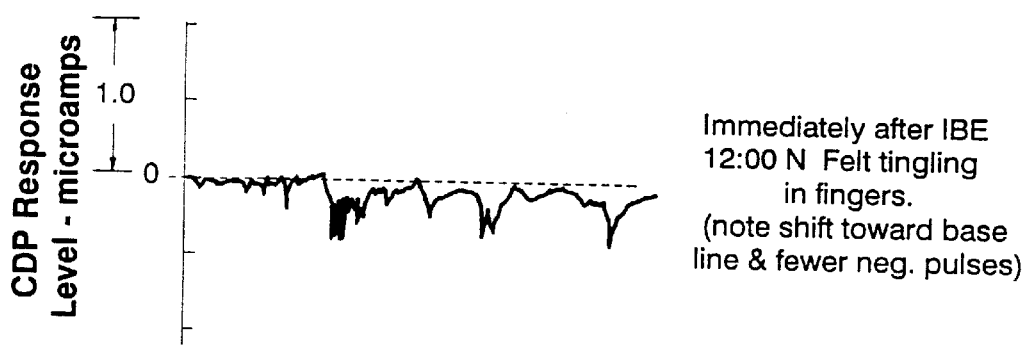

By 12:00 Noon, after the treatment, the subject reported a lessening of pain but a tingling in the fingers and produced the CDP trace in FIG. 14B, with fewer spikes and a general movement of the CDP trace in the positive direction toward the baseline.

Figure 14C:
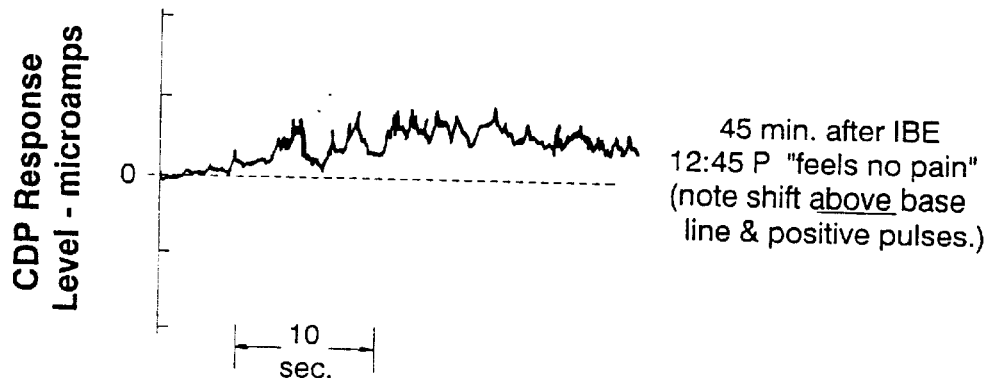

Forty-five minutes later, the CDP trace in FIG. 14C was recorded after the subject reported feeling no pain nor tingling. FIG. 14C shows a rise of the subject's CDP traces above the baseline into positive values.

Figure 14D:
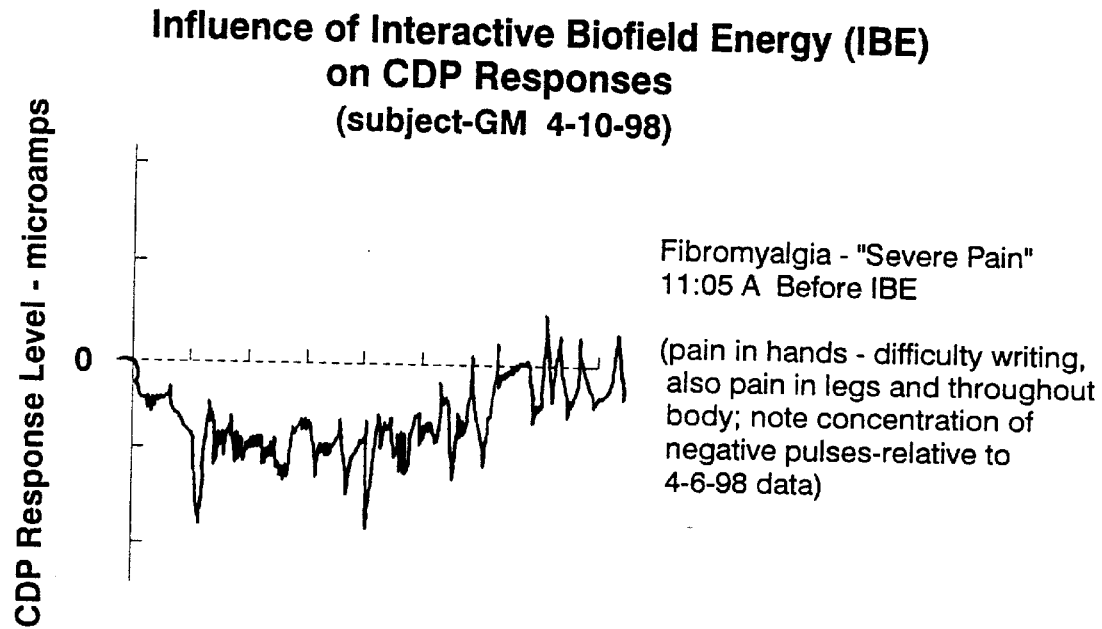

FIG. 14D shows the record of a trace recorded by the same subject four days later while reporting severe pain throughout the body. It contained many large spikes and occurred mostly below the baseline in the negative region.

Figure 14E:
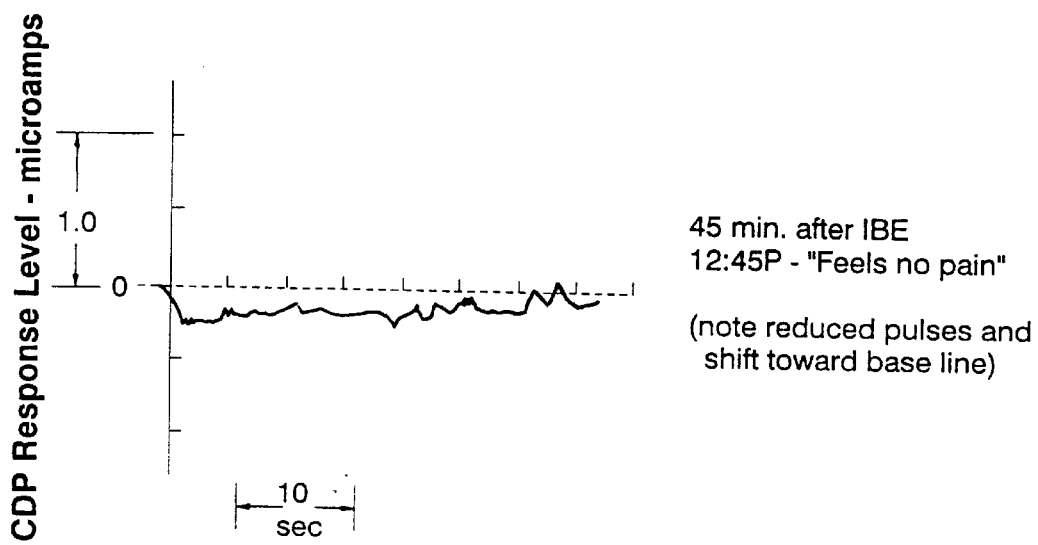

Forty-five minutes after receiving another treatment of hands on healing the subject reported being pain free and produced the CDP trace in FIG. 14E. This trace moved most of the way back toward the baseline and contained no large negative spikes.

Figure 14F:
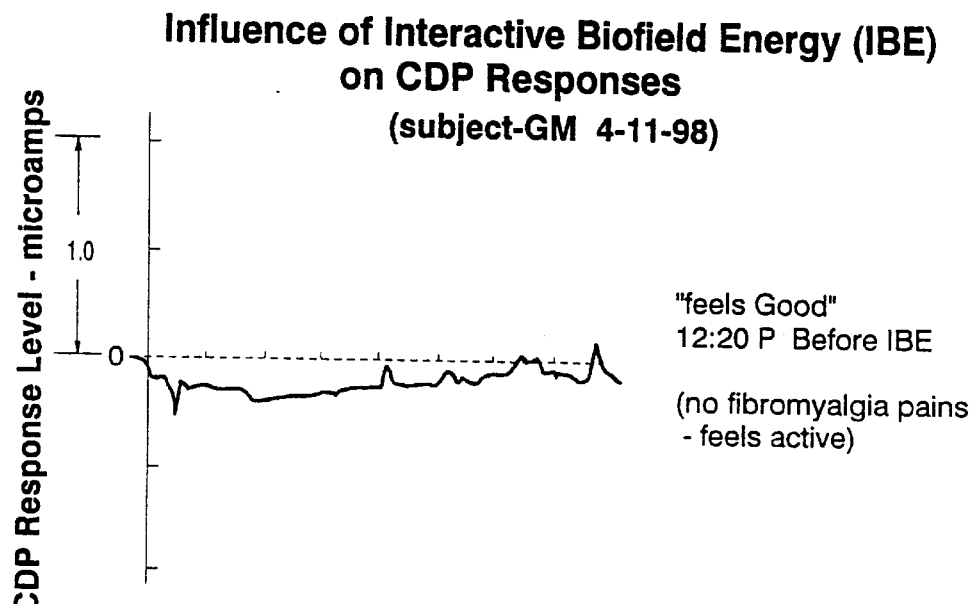

By contrast, FIG. 14F was taken from the same subject on a day without pain. Though the CDP trace was slightly negative, there was an absence of large spikes.

Figure 14G:
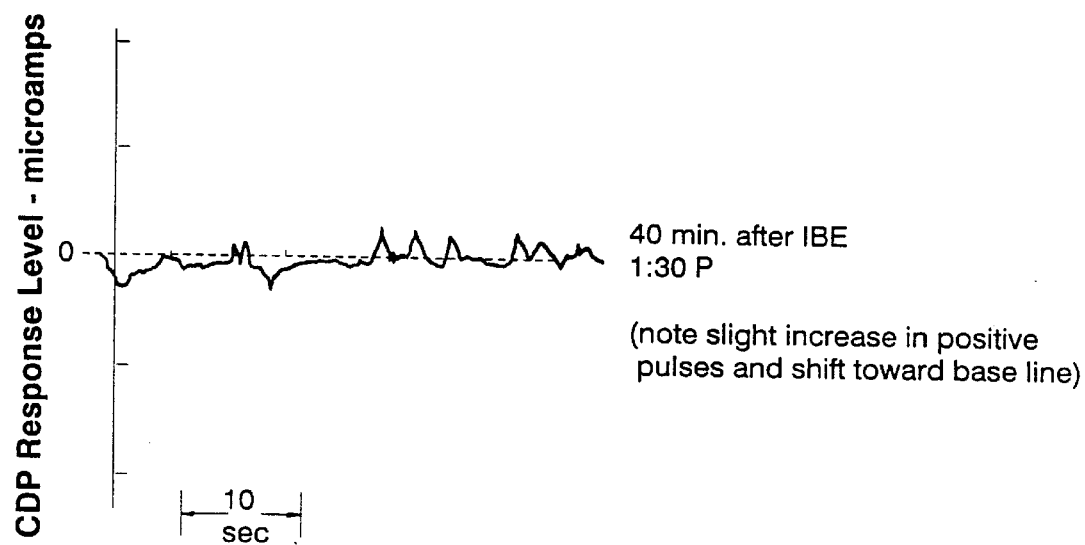

A treatment of the same kind of hands on healing was applied and one hour later the CDP trace in FIG. 14G showed a slight movement in the positive direction but otherwise no large change.

This indicates that the differences shown above before and after treatment of this hands on healing therapy was not an artifact of the therapy but was representative of reduced pain from fibromyalgia. In summary, traces in a subject, which contained large spikes and occurred below the baseline were typical of a subject in pain. Thus the present invention was shown to bring a degree of objectivity and quantification to the difficult study of pain and its treatment.

Example 8

The present invention can also be used to help assess the optimal dose for Ritalin in subjects with Attention Deficit Disorder (ADD). A debate within the medical community concerns the size of the minimal effective dose of Ritalin for control of ADD, with some believing that doses prescribed for children may sometimes be unnecessarily high.

Figure 15A:
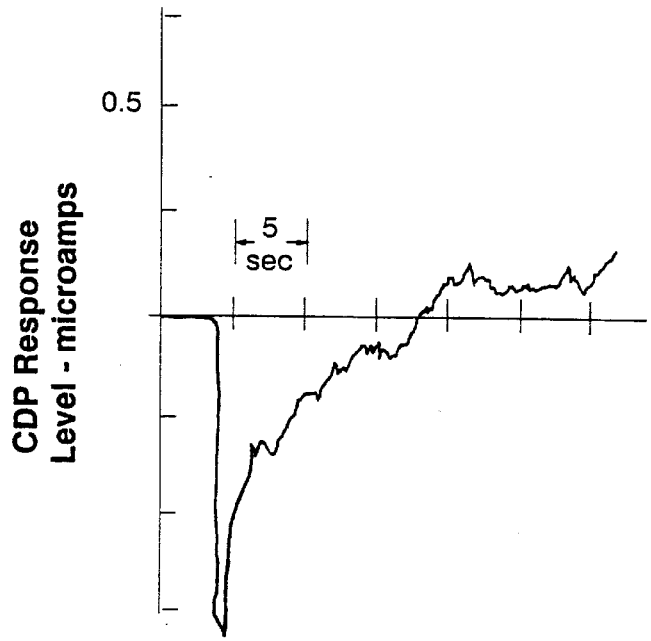
FIGS. 15A–15C show Charge Density Pulse (CDP) readings of a human subject discussed in Example 8 herein, also using the flat plate embodiment shown in FIG. 3A, in connection with the treatment of Attention Deficit Disorder (ADD) with Ritalin.
Figure 15B:
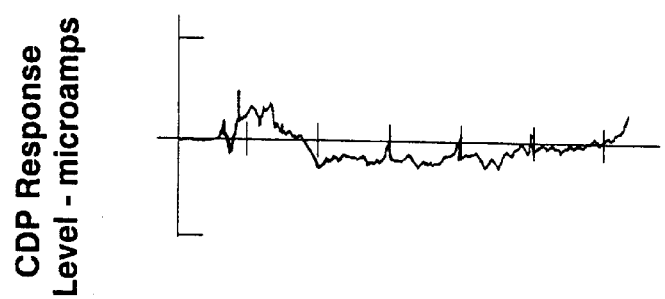
Figure 15C:
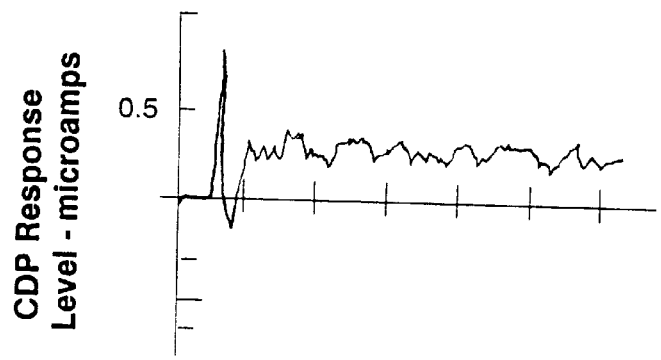

In this Example, a 51 year old man with ADD placed his palms and fingers on the flat aluminum plate electrodes, connected as previously described in FIG. 3A, to a resistor and chart recorder shortly before and after taking his prescribed dose of Ritalin and showed the differences illustrated in FIGS. 15A, 15B and 15C.

FIG. 15A shows that the train of electric Charge Density Pulses produced before Ritalin ingestion showed a high amplitude negative Pa, with the pulses only rising above the baseline halfway through the trace.

Thirty minutes after ingestion of his regular dose of Ritalin the subject produced a completely different trace as shown in FIG. 15B, virtually all of which is above the baseline and with Pa amplitudes less than half that of the Pa before Ritalin ingestion. As shown in FIG. 15C, seventy minutes after ingestion of Ritalin the Pa was still small and positive, though some of the CDP trace occurred below the baseline.

Such a system of measurement allows the physician to experiment with finding the smallest effective dose if he or she so desires, without having to depend entirely on the subjective reports of ADD subjects who are often young children.

Example 9

Figure 16:
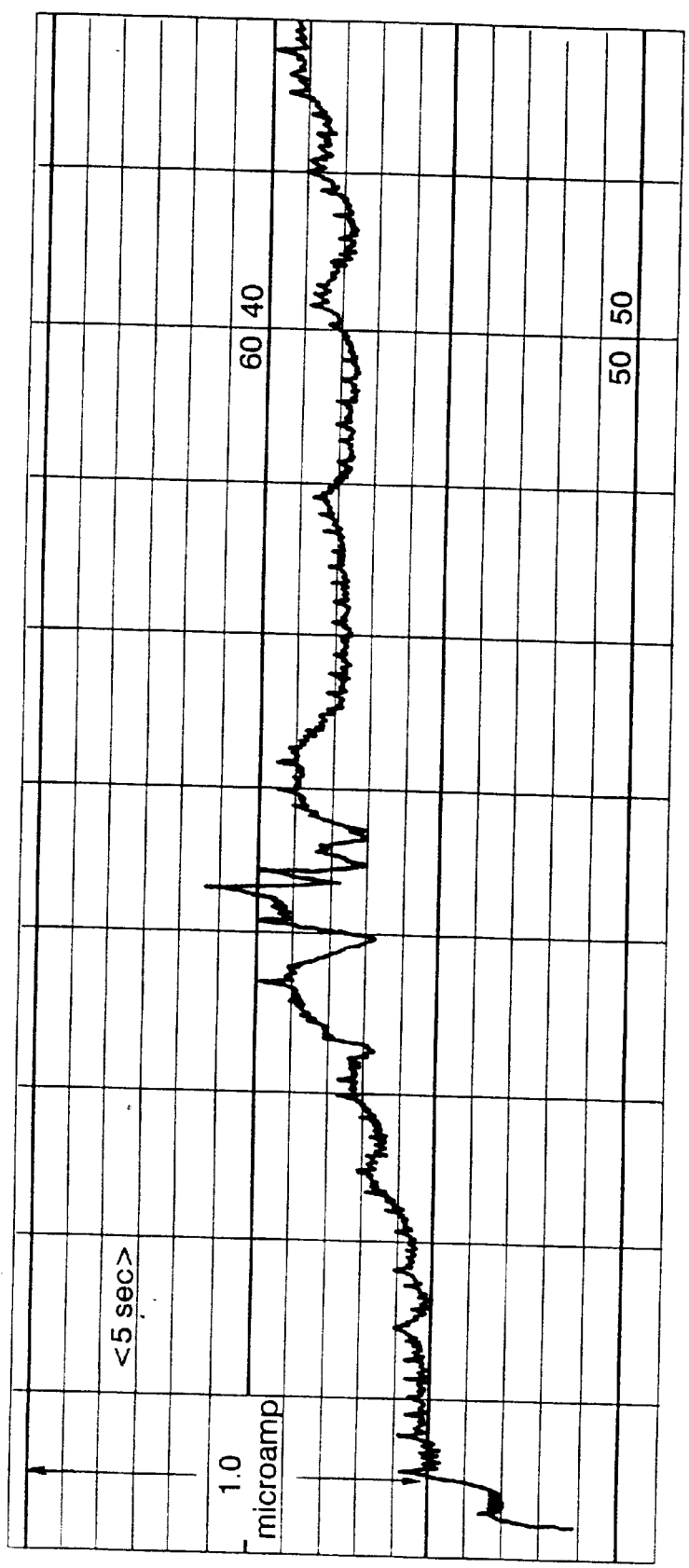

An unusual, periodic bioelectric pulse rate has shown to be associated with serious spinal trauma. By subjects placing their palms and fingers on the flat aluminum plate electrodes which were connected to a chart recorder and joined across a resistor as previously described in FIG. 3A, repeated pulse traces in a dozen individuals showed small spikes of identical amplitude at a frequency of approximately 1.4 to 1.7 Hz overlain on the larger components of the pulse trace, as shown in FIG. 16.

In over fifty subjects measured, only the twelve with severe spinal trauma in their past showed this distinctive feature.

With several of the individuals, the injury had occurred so far in their past or early in their lives that they failed to remember it when questioned and the existence of the injury was confirmed by family members.

In chiropractic practice, for example, initial detection of this feature could suggest the possibility of a history of such trauma and indicate the need for further investigation—which would, most likely include a full history, physical, and radiological investigation—before developing a treatment plan. It is not intended that the present invention be used alone for such follow-up investigatory purposes.

Example 10

FIGS. 17A and 17B show Charge Density Pulse (CDP) readings using the cylindrical rod electrodes shown in FIG. 4, to search for evidence of body trauma and which were particularly useful for analyzing individuals incapable of communication, such as the very young or stroke victims.

In this case a 76 year old woman suffered a severe blow to her right foot, which produced a bone bruise and a feeling of partial numbness.

In FIG. 17A, a brass cylindrical probe electrode of the type described above was placed on the right foot at the top of the arch on the outside of the foot while the left palm was placed on the cathode aluminum plate electrode as a reference electrode. Lead wires were connected to a chart recorder as previously described. FIG. 17B shows the bioelectric pulse trace, which resulted therefrom.

Then the process was reversed to measure the uninjured ankle, giving the trace recorded in FIG. 17C. The amplitude of the trace in the injured foot is approximately 75% depressed when compared to the uninjured foot.

In the medical community, comparisons between symmetrically opposite body parts is a standard technique. Thus the present invention provides the investigator with a simple, inexpensive, and non-invasive method to search for possible injuries in a non-communicative patient.

It is further noted that the other modifications may be made to the present invention, without departing from the scope of the invention, as noted in the appended Claims.

We claim:

1. A method of characterizing the state of the bioelectric field originating in organisms by detecting and recording a specific type of spontaneously-generated electric charge pulses induced in metal electrodes by the living tissue of animals or plants, comprising the steps of:

passively detecting in the absence of any external voltage source the electric energy produced by a living source as said living source interacts with a crystalline lattice of a pair of conductive electrodes to produce a train of oscillating pulses, measuring the amplitude of said pulses as said pulses decay as a linear function of log-time, and, analyzing said pulses to detect changes in said living source over time.

2. The method as in claim 1, further comprising the steps of recording changes in charge density pulse dissipation before and after one of medical, chiropractic and therapeutic treatment of said living animal source.

3. A method of characterizing the state of the bioelectric field of a human being comprising the steps of:

placing a pair of conductive electrodes in the form of plates against the palms of the hands of a person, respectively, with an air gap between said plates, said plates being large enough to cover the complete palm and fingers of each hand;

connecting a conductor to each of said plates;

passively detecting in the absence of any external voltage source the electric energy sensed by said plates generated by said person to produce a train of oscillating pulses, measuring the amplitude of said pulses as said pulses decay as a linear function of log-time, generating and recording a charge density pulse trace;

analyzing said pulse trace to detect changes in said person over time.

4. The method of claim 3 in which said plates are circular and spaced apart about 8 cm.

5. The method of claim 3 in which said plates are semi-polished.

6. The method of locating an internal injury in a body of a person comprising the steps of:

placing the tip of a stationary electrode in contact with a reference point on the body of said person, said stationary electrode being connected through a conductor to a device capable of measuring voltages generated from within said body;

placing a movable electrode in contact with a series of other points on said body, said movable electrode being connected through a conductor to said device;

said device passively detecting in the absence of any external voltage source the electric energy produced by said person as said movable electrode is moved from point to point on said body to produce a train of oscillating pulses, measuring the amplitude of said pulses as said pulses decay as a linear function of log-time, generating and recording a charge density pulse trace; and analyzing said pulse trace to detect the presence of any injury within said body.

7. The method of claim 6 in which said electrodes are cylindrical in shape with flat semi-polished tissue-contacting ends.

8. The method of claim 7 in which said reference point is the center of a forehead of said person.

9. The method of tracking the healing of an injury in a body of a person comprising the steps of:

placing a tip of a stationary electrode in contact with a reference point on the body of said person, said stationary electrode being connected through a conductor to a device capable of measuring voltages generated from within said body;

placing a movable electrode in contact with an area of skin covering said injury, said movable electrode being connected through a conductor to said device;

said device passively detecting in the absence of any external voltage source the electric energy produced by said person to produce a train of oscillating pulses, measuring the amplitude of said pulses as said pulses decay as a linear function of log-time, generating and recording a charge density pulse trace; and analyzing said pulse trace to detect healing of said injury.

10. A method of evaluating objectively a treatment for the relief of pain in a person comprising the steps of:

a) placing a pair of conductive electrodes in the form of plates against the palms of hands of a person, respectively, with an air gap between plates, said plates being large enough to cover the complete open palm and fingers of each hand;

b) connecting a conductor to each of said plates;

c) passively detecting in the absence of any external voltage source the electric energy produced by said person to produce a train of oscillating pulses, d) measuring the amplitude of said pulses as said pulses decay as a linear function of log-time, e) generating and recording a charge density pulse trace;

f) treating the person for pain;

g) repeating steps a) through e); and h) analyzing said pulse traces to detect changes in said charge density pulse traces over time as an objective measure of the relief of pain in said person.

* * * * *